United States Patent
Bao et al.

(10) Patent No.: US 10,661,239 B2
(45) Date of Patent: May 26, 2020

(54) CATALYTIC REACTOR CONFIGURATION, PREPARATION AND METHOD OF DIRECT SYNTHESIS OF ETHYLENE THROUGH OXYGEN-FREE CATALYSIS OF METHANE

(71) Applicant: DALIAN INSTITUTE OF CHEMICAL PHYSICS, CHINESE ACADEMY OF SCIENCES, Dalian (CN)

(72) Inventors: Xinhe Bao, Dalian (CN); Xiaoguang Guo, Dalian (CN); Guangzong Fang, Dalian (CN); Xiulian Pan, Dalian (CN); Jingheng Meng, Dalian (CN); Qinqin Yu, Dalian (CN); Dali Tan, Dalian (CN)

(73) Assignee: DALIAN INSTITUTE OF CHEMICAL PHYSICS, CHINESE ACADEMY OF SCIENCES, Dalian (CN)

( * ) Notice: Subject to any disclaimer, the term of this patent is extended or adjusted under 35 U.S.C. 154(b) by 28 days.

(21) Appl. No.: 16/300,188

(22) PCT Filed: Mar. 22, 2017

(86) PCT No.: PCT/CN2017/077614
§ 371 (c)(1),
(2) Date: Nov. 9, 2018

(87) PCT Pub. No.: WO2017/185920
PCT Pub. Date: Nov. 2, 2017

(65) Prior Publication Data
US 2019/0143288 A1    May 16, 2019

(30) Foreign Application Priority Data
Apr. 29, 2016  (CN) .......................... 2016 1 0286107

(51) Int. Cl.
*B01J 7/00* (2006.01)
*C07C 2/84* (2006.01)
(Continued)

(52) U.S. Cl.
CPC ............... *B01J 7/00* (2013.01); *B01J 10/007* (2013.01); *B01J 12/007* (2013.01); *B01J 15/00* (2013.01);
(Continued)

(58) Field of Classification Search
CPC ... B01J 35/06; B01J 23/10; B01J 23/34; B01J 35/0013; B01J 21/066; B01J 21/10;
(Continued)

(56) References Cited

U.S. PATENT DOCUMENTS

| 8,921,256 B2 | 12/2014 | Cizeron et al. |
| 2009/0259063 A1* | 10/2009 | Lang .................... B01J 19/0093 556/476 |

(Continued)

FOREIGN PATENT DOCUMENTS

| CA | 28370201 A | 11/2012 |
| CN | 101502757 A | 8/2009 |

(Continued)

OTHER PUBLICATIONS

Shuqi Ma et al., "Recent progress in methane dehydroaromatization: From laboratory curiosities to promising technology", Journal of Energy Chemistry 22(2013)1-20.
(Continued)

*Primary Examiner* — Sharon Pregler
(74) *Attorney, Agent, or Firm* — Enshan Hong; VLP Law Goup LLP

(57) ABSTRACT

A reactor configuration comprises an inlet section I, a preheating section II, a transition section III, a reaction section IV and an outlet section V; except for the preheating
(Continued)

section II and the reaction section IV, the existence of the inlet section I, the transition section III and the outlet section V depends on reaction conditions; and the process realizes no coke deposition synthesis of methane and high selectivity synthesis of ethylene. The methane conversion rate is 20-90%; ethylene selectivity is 65-95%; propylene and butylene selectivity is 5-25%; aromatic hydrocarbon selectivity is 0-30%; and coke deposition is zero.

33 Claims, 1 Drawing Sheet

(51) Int. Cl.
| | | |
|---|---|---|
| | *B01J 15/00* | (2006.01) |
| | *B01J 12/00* | (2006.01) |
| | *B01J 10/00* | (2006.01) |
| | *B01J 19/00* | (2006.01) |
| | *B01J 19/02* | (2006.01) |
| | *B01J 19/24* | (2006.01) |
| | *C07C 2/76* | (2006.01) |
| | *C23C 16/40* | (2006.01) |

(52) U.S. Cl.
CPC .......... *B01J 19/0013* (2013.01); *B01J 19/02* (2013.01); *B01J 19/2415* (2013.01); *C07C 2/76* (2013.01); *C07C 2/84* (2013.01); *C23C 16/402* (2013.01); *B01J 2219/0093* (2013.01); *B01J 2219/00159* (2013.01); *B01J 2219/00835* (2013.01); *C07C 2521/08* (2013.01); *C07C 2521/18* (2013.01); *Y02P 20/52* (2015.11)

(58) Field of Classification Search
CPC ...... B01J 23/22; B01J 37/0018; B01J 37/031; B01J 37/08; B01J 37/10; B01J 23/02; B01J 23/04; B01J 23/30; B01J 2523/00; B01J 29/06; B01J 35/026; B01J 35/04; B01J 35/1009; B01J 35/1014; C07C 2/84; C07C 11/04; C07C 5/48; C07C 2523/02; C07C 2523/10; C07C 2523/30; C07C 2523/34; C07C 2521/10; C07C 2523/04; C07C 11/06; C07C 2523/22; C07C 2/10; C07C 2521/06; C07C 2523/75; C07C 2527/224; C07C 2/06; C07C 2/82; C07C 11/02; C07C 11/107
See application file for complete search history.

(56) References Cited

U.S. PATENT DOCUMENTS

| | | |
|---|---|---|
| 2012/0041246 A1 | 2/2012 | Scher |
| 2013/0165728 A1 | 6/2013 | Zurcher |
| 2014/0121433 A1 | 5/2014 | Cizeron |

FOREIGN PATENT DOCUMENTS

| | | |
|---|---|---|
| CN | 102513032 A | 6/2012 |
| CN | 102553813 A | 7/2012 |
| CN | 204051661 U | 12/2014 |
| CN | 104148101 B | 12/2016 |
| CN | 106914243 A | 7/2017 |
| DE | 4428343 A1 | 2/1996 |

OTHER PUBLICATIONS

International Search Report dated Jul. 10, 2017 for the related international patent application No. PCT/CN2017/077614.
Written Opinion dated Jul. 10, 2017 for the related international patent application No. PCT/CN2017/077614.

* cited by examiner

CATALYTIC REACTOR CONFIGURATION, PREPARATION AND METHOD OF DIRECT SYNTHESIS OF ETHYLENE THROUGH OXYGEN-FREE CATALYSIS OF METHANE

RELATED APPLICATIONS

This is a U.S. national stage of international application No. PCT/CN2017/077614 filed on Mar. 22, 2017, which claims priority from China Patent Application No. 201610286107.6 filed on Apr. 29, 2016, the entire content of which is incorporated herein as reference.

TECHNICAL FIELD

The present invention relates to a catalytic reactor configuration, preparation and a method of direct synthesis of ethylene through oxygen-free catalysis of methane. The process realizes efficient conversion of methane, high selectivity synthesis of ethylene, high catalyst stability and zero carbon deposition.

BACKGROUND

Development and effective utilization of natural gas (methane) resource represent the development direction of the contemporary energy structure and is also one of important ways of ensuring sustainable development and energy greening. In recent years, western developed countries have made breakthrough in the development aspect of shale gas and "combustible ice", resulting in a "shale gas revolution". In China, shale gas resources have many types and are distributed centrally relatively. The recoverable resource potential is 25 trillion cubic meters (Qinghai-Tibet region excluded), which is equivalent to that of conventional natural gas for land in China and close to 24 trillion cubic meters of America. The "Twelfth Five-year plan" in China has deployed in the development field of the shale gas to obtain technical breakthrough in several different kinds of shale oil and gas regions and to preliminarily establish productivity with economic benefits.

However, how to efficiently use gaseous hydrocarbon resources (methane) has already become an important link that restricts the development of energy industry of China. It reignites the world-wide interest to convert such abundant resources into fuel and high-added-value chemicals (especially light olefins), and also an important step for improving the energy structure of China. Light olefins, such as ethylene, etc., are very important raw material or intermediates in the chemistry and chemical engineering process. Traditional light olefins (C2-C4) mainly come from the petrifaction process of naphtha cracking, etc., so that the production of the olefins has already become a symbol for measuring the petrochemical production level of one country and region. As petroleum resources are increasingly exhausted, it is a focus of current study to explore a method for making the light olefins in a non-traditional route. Accordingly, some typical substitute routes arise at the historic moment, such as the route of starting from synthetic gas and further converting methanol or dimethyl ether to obtain the light olefins, but this route has complicated process and lower atom economy. To shorten the reaction route, a large number of studies are carried out on direct synthesis of the light olefins through a Fischer-Tropsch route starting from the synthetic gas. However, the above substitute route must consume CO or $H_2$ to remove O in CO, which may inevitably cause C atom utilization rate lower than 50%. In spite of expensive productivity input, heavy $CO_2$ emission and atom utilization rate lower than 50%, the indirect process still occupies a dominant status in application of natural gas industry.

In contrast, direct conversion of natural gas has enormous economic potential and is more environmentally friendly. However, direct conversion of natural gas remains a difficult problem in the chemistry and chemical engineering process. The essential component of natural gas is methane. The bond energy of C—H bond is as high as 434 kJ/mol, while the methane molecule itself almost has no electron affinity. In addition, ionization energy is large and polarization rate is small. Therefore, activation of the C—H bond of methane is regarded as a "holy grail" of chemistry and even chemistry field. Keller and Bhasin has reported activation of the C—H bond of methane under the participation of $O_2$. Their pioneering work ignites the world-wide enthusiasm on studying preparation of ethylene from oxidative coupling of methane under high temperature (>1073K), in which hundreds of catalysis materials are synthesized and tested. The study has reached the peak in the 90s. In the oxidative coupling process, because of the introduction of molecular oxygen ($O_2$), over oxidation of methane and its products are inevitably caused, thereby producing a great number of products with stabler thermodynamics than methane, such as $CO_2$ and $H_2O$ and finally causing relatively low C atom utilization efficiency. Due to the bottleneck of the development of new material and raw catalysts, the development of the oxidative coupling process of methane stagnates. So far, new technologies with economic feasibility are rarely reported. A recent study proposes that gas-phase S with weak oxidability substitutes for molecular oxygen $O_2$ to generate an oxidative coupling reaction of methane. At temperature of 1323K (reaction gas: 5% $CH_4$/Ar), an optimal $PdS/ZrO_2$ catalyst can realize 16% of methane conversion; however, $C_2H_4$ selectivity is only about 20%, but can produce a great number of $CS_2$ and $H_2S$. The above study reveals that oxygen (or oxidizer) assisted methane activation inevitably causes over oxidation.

Therefore, direct conversion of methane without oxygen (or without oxidizer) is considered to be an ideal activation and conversion route of methane. Under the condition of no oxygen (or no oxidizer), over oxidation of methane or products can be effectively avoided, thereby inhibiting emission of greenhouse gas $CO_2$ and then increasing C atom utilization rate. The challenges of preparing ethylene by direct catalytic conversion of methane are that: 1) the first C—H bond is broken through controllable methane activation; 2) depth dehydrogenation on a catalyst surface is suppressed; 3) generation of greenhouse gas $CO_2$ and carbon deposition is avoided, wherein 1 and 2 are for the catalyst, while 3 is for the reaction process. Over oxidation of products of the aerobic process is inevitable, resulting in inevitable generation of $CO_2$. Only the oxygen-free process can avoid producing $CO_2$, but is easy to produce carbon deposition. Therefore, a study on how to avoid carbon deposition becomes a current focus of the oxygen-free process. The key to solve the carbon deposition problem is to understand a source of carbon deposition. By taking an oxygen-free aromatization process as an example, the carbon deposition mainly comes from: methane is deeply dehydrogenated to generate carbon deposition ("graphite-like carbon deposition") on the surface of Mo species of the catalyst; in the diffusion process, the products are cyclized and coupled on B acid site of a duct or orifice of a support and zeolite to generate carbon deposition ("polyaromatic carbon deposition"). Therefore, three challenges of preparing ethylene by direct catalytic conversion of methane are design and construction of the catalyst.

In 1993, researchers from Dalian Institute of Chemical Physics (DICP) reported $CH_4$ dehydroaromatization in a continuous flow pattern on the Mo/HZSM-5 catalyst for the first time. At 973K and normal pressure, $CH_4$ conversion is about 6% and aromatics selectivity is greater than 90% (exclusive of carbon deposition in the reaction), forming an important milestone of study on $CH_4$ dehydroaromatization process. In the past decades, the study work of multinational scientists mainly focuses on preparation, development, reaction and deactivation mechanism of the catalyst. Nevertheless, industrial applications are restricted by the rapid carbon deposition and deactivation of the catalyst.

Recently, a composite catalyst prepared by American siluria company (US201241246, US2013165728, US2014121433, CA2837201 and U.S. Pat. No. 8,921, 256B29) using a biological template method generates 26% of methane conversion and 52% of ethylene selectivity in the oxidative coupling reaction at 600-650° C. At present, the company is performing pilot production, and is expected to conduct industrialized demonstration in 2017-2018. For preparation of methanol or formaldehyde from selective oxidation of methane, because the oxidation velocity of target products of methanol and formaldehyde is much higher than that of methane as raw material, the reaction selectivity is lower and the products have hardly scale application prospect.

Two patents (application numbers: 201310174960.5 and 201511003407.0) have been applied earlier. These two patents mainly apply for a metal doped silicon-based catalyst so as to realize the process of producing alkene through catalytic conversion of methane by a fixed bed or fluidized bed or mobile bed by placing the catalyst into a reactor. The two methods have the disadvantages of large pressure drop of catalyst bed layer, poor heat conduction of catalyst, large temperature difference of bed layer, harsh preparation condition of catalyst, difficult scaleup, etc.

Therefore, the purpose of the present invention is to lattice-dope active metal or non-metal component into the inner wall of a quartz or silica carbide reactor with a unique shape, or lattice-dope active metal or non-metal component into quartz or silica carbide and coat on the inner wall of the reactor, so that the catalyst and the reactor become a whole. Compared with the above two patents, the method has the following advantages:

1) In the high temperature melting process, internal temperature difference of the catalyst is small, and the repeatability is good. The traditional preparation of catalysts from the laboratory (gram level) to the industrial level (tonnage level) requires many years of repeated stepwise scaleup. The duration of the process is determined by the severity of the preparation conditions of the catalysts. At present, the catalyst needs to undergo a high temperature melting process of 1800-2200° C. The temperature can realize uniform melting for a small number of (gram level) catalysts, but if gram level is scaled up to kilogram level or tonnage level, the internal temperature difference will increase and the repeatability of the catalyst will become poor.

2) For the reaction process, there is no axial or radial temperature difference of the catalyst bed. Because after the catalyst is filled in the reactor, due to poor thermal conductivity of the catalyst, the radial temperature difference of the bed increases (the temperature presents a decreasing trend from the reactor wall to the center). Thus, more heat shall be supplied to reach the reaction temperature at the center of the catalyst bed, resulting in the problems of heat loss and more side reactions at the near wall section (high temperature end).

3) There is no pressure drop in the bed, and the reaction process is more stable.

4) The non-oxidative synthesis of ethylene from methane is a free radical reaction. The catalyst placed on the wall surface provides a larger space for the subsequent gas phase process, which can greatly improve the conversion rate of the methane.

5) It can solve the scaleup problem of catalyst. At present, the pipe diameter of an industrial shell and tube reactor is usually about 50 mm. Meanwhile, the tube diameter of a laboratory microreaction device is about 20 mm. Namely, the optimized catalyst obtained in the laboratory can be easily amplified to 50 mm, so as to avoid the problem of catalyst scaleup.

The process is easier for industrial amplification. At present, the industrialized methane reforming and ethane pyrolysis adopts the shell and tube reactors (no catalyst bed). Namely, the adopted shell and tube reactors are directly replaced with the catalytic reactor of the present invention to realize production of ethylene through methane.

SUMMARY OF THE INVENTION

The present invention to solve the technical problem is: to overcome defects of the prior art and to provide a catalytic reactor configuration, preparation and a method of direct synthesis of ethylene through oxygen-free catalysis of methane. The present invention has the characteristics of long life of catalysts, high stability of redox and hydrothermal conditions at high temperature, high conversion rate of methane, high selectivity of products, zero coke deposition, no scaleup of catalyst, small industrialization difficulty, easy separation of products, good process reproducibility, safe and reliable operation. etc.

The so-called catalytic reactor in the present invention refers to directly lattice-doping active components to the inner wall of a quartz or silica carbide tube; or coating Si-based material lattice-doped by the active components to the inner wall of the quartz tube or the silica carbide tube to form a dopant thin layer, and finally melting at high temperature to form a catalytic reactor. The so-called oxygen-free conversion of methane refers to a manner that methane is converted directly in absence of oxidizer (such as oxygen, elemental sulfur, sulphur dioxide, etc.).

The catalytic reactor refers to lattice-doping metal atoms or nonmetallic atoms to the inner wall of a quartz or silica carbide reaction tube. The doping refers to lattice doping. The so-called lattice doping is that the dopant metallic elements form a chemical bonding with some elements in the metallic elements or nonmetallic elements, which will lead to the dopant metallic elements being confined in the lattice of the doped base material, resulting in specific catalytic performance.

The metal doping amount of the metal lattice-doped catalysts are more than 10 ppm, but less than or equal to 0.1 wt. % of total weight (100%) of the catalyst; the metal doping amount of the nonmetal lattice-doped catalysts shall be more than 10 ppm, but less than or equal to 1 wt. %. The metal doping amount of the metal lattice-doped catalysts is preferably 100 ppm-0.1 wt. %. The doping amount of the metal or metal compounds in the Si material is 0.01-0.5 wt. %. If the doping amount is higher than 1 wt. %, it will be difficult to form lattice doping.

The so-called amorphous-molten-state materials are that the metal and silicon-based materials are all in a molten state in the preparation process, and then amorphous materials with long-range disorder and short-range order are formed after being rapidly cooled.

The dopant metallic elements comprise: lithium, magnesium, aluminum, calcium, strontium, barium, titanium, manganese, vanadium, chromium, iron, cobalt, nickel, zinc, germanium, tin, gallium, zirconium, gold, lanthanum, cerium, praseodymium, neodymium, europium, erbium and ytterbium.

The dopant nonmetallic elements comprise: boron and phosphorus.

For the dopant metallic elements, the states of the dopant metal are one or more of metal oxides, metal carbides and metal silicates. For the dopant nonmetallic elements, the states of the dopant non-metal are metal oxides.

The catalysts are silicon-based materials that comprise Si bonded with one or more than two of C and O as the main body, which is obtained by doping in its lattice metal dopants, forming a molten state, and solidifying the molten material.

The precursors (states for pre-dopant metallic elements) of dopant metallic elements include one or more than two of nitrates, chloride, organic acid salts of C atom number from 1 to 2 and organic alcohol salt of C atom number from 1 to 2. The precursors (states for pre-dopant metallic elements) of dopant non-metallic elements include one or more than two of chloride or oxygen chloride.

The silicon-based material of the dopant metallic elements is the inner wall of the reactor, and mainly includes $SiO_2$ or $SiC$.

As shown in FIG. 1, a catalytic reactor configuration at least comprises a preheating section and a reaction section, wherein the reaction section refers to directly lattice doping active components to the inner wall of a quartz tube or a silica carbide tube, or coating Si-based material lattice-doped by the active components to the inner wall of the quartz tube or the silica carbide tube to form a dopant thin layer, and the quartz tube or the silica carbide tube with the inner wall which is directly doped or doped by coating is called as the reaction section; reaction conditions of the catalytic reactor configuration also include an inlet section located at the front of the preheating section or a transition section located between the preheating section and the reaction section or an outlet section located at the rear of the reaction section, or simultaneously include the above inlet section, the transition section and the outlet section; and one or more sections of the inlet section, the preheating section, the transition section, the reaction section and the outlet section are respectively manufactured and connected.

The length II of the preheating section and the length IV of the reaction section are respectively 50-2000 mm. The inner diameter A of the inlet section, the inner diameter B of the preheating section, the inner diameter C of the transition section, the inner diameter D of the reaction section and the inner diameter E of the outlet section are respectively 3-500 mm, and preferably 5-200 mm. The length I of the inlet section, the length III of the transition section and the length V of the outlet section are not larger than 5000 mm, and 0<I+III+V<5000 mm. The length I of the inlet section, the length II of the preheating section, the length III of the transition section, the length IV of the reaction section and the length V of the outlet section satisfy: 0.1 m<I+II+III+IV+V<10 m.

Moreover, the inner diameter of each section needs to satisfy: D>A=B=C=E, or D=B>A=C=E, or B>D>A=C=E, or D>B>A=C=E, or A=B>D>C=E, or A=B>D>C>E, or A=B=C=D=E, or A=E>B=C=D, or A=C=E>B=D.

The thickness of the dopant thin layer is 1 nm-1 mm, preferably 1 nm-0.05 mm, more preferably 1 nm-0.005 mm and further preferably 5 nm-50 nm.

The reaction section in the catalytic reactor is prepared through the following solid phase doping technology. The solid phase doping technology is a modified chemical vapor deposition (MCVD) method which uses an MCVD apparatus.

The purpose of the following preparation process of the reaction section is to improve the dispersion of the metallic elements in the silicon-based materials, and to dope the metallic elements more effectively in the lattice of amorphous-molten-state materials made from Si bonded with one or more than two of C and O element.

The solid phase doping technology comprises the modified chemical vapor deposition (MCVD) method.

The first method: at 1-3 atmospheric pressure, bringing silicon tetrachloride liquid and nonmetallic chloride which is gas-phase doped at 50-500° C. under the drive of support gas to enter the MCVD apparatus to react at 1400-1650° C.; conducting vapor deposition of $SiO_2$ thin layer with a thickness of 0.01-100 micrometers on the inner wall of the reaction section IV; subsequently immersing the reaction section IV at 20-80° C. into metal salt (one or more than two of nitrate, soluble halogenide, soluble sulphate, soluble carbonate, soluble calcium phosphate, soluble organic alkoxide with C number of 1-2, or organic acid salt with C number of 1-2) doped aqueous solution for 0.1-20 hours; then melting the reaction section IV at 1800-2200° C. to obtain the corresponding metal lattice doped reaction section of the inner wall; forming a dopant thin layer with a thickness of 1 nm-1 mm on the inner wall of the reaction section; then immediately cooling; and curing to obtain the reaction section of the catalytic reactor.

The second method: at 1-3 atmospheric pressure, bringing silicon tetrachloride liquid and gas-phase-doped volatile metal salt (one or more than two of metal chloride, organic alkoxide with C number of 1-2, and organic acid salt with C number of 1-2) which is gasified at 50-950° C. or nonmetallic chloride which is gas-phase doped at 50-500° C. under the drive of the support gas (oxygen or helium) to enter an MCVD apparatus to react with oxygen at 1400-1650° C.; depositing for 10 min-2 h and then conducting vapor deposition for the dopant thin layer on the inner wall of the reaction section; subsequently melting at 1800-2200° C. to obtain the corresponding metal lattice doped reaction section of the inner wall; forming a dopant thin layer with a thickness of 1 nm-1 mm on the inner wall of the reaction section; then immediately cooling; and curing to obtain the reaction section of the catalytic reactor.

The third method: at 1-3 atmospheric pressure, bringing silicon tetrachloride liquid and normal-temperature liquid metal chloride (tin tetrachloride, titanium tetrachloride and germanium tetrachloride) or normal-temperature liquid nonmetallic chloride or oxygen chloride (boron trichloride and phosphorous oxychloride) under the drive of support gas to enter an MCVD apparatus to react at 1400-1650° C.; depositing for 10 min-2 h and then conducting vapor deposition for the dopant thin layer on the inner wall of the reaction section; subsequently melting at 1800-2200° C. to obtain the corresponding metal lattice doped reaction section of the inner wall; forming a dopant thin layer with a thickness of 1 nm-1 mm on the inner wall of the reaction section; then immediately cooling; and curing to obtain the reaction section of the catalytic reactor.

The reaction section of the catalytic reactor can also be prepared by a solid-liquid phase doping technology. A sol-gel method is combined with a high temperature melting technology. The purpose of the following preparation process is to improve the dispersion of the metallic elements in the silicon-based materials, and to dope the metal elements more effectively in the lattice of amorphous-molten-state materials made from Si bonded with one or more of C and O element.

At room temperature, the inner wall of the reaction section IV is etched using HF or NaOH solution for 1-48 h, or the inner wall of the reaction section IV is ground for 0.5-4 h using SiC particles of 40-100 meshes; meanwhile, a mixed solution of metal salt/silicate/water is prepared; the mixed solution is uniformly covered on the inner wall of the etched reaction section; sol-gel reaction is conducted at 20-120° C.; after sol and gel treatment of the inner wall of the reaction section IV for 0.2-96 h, melting is conducted at 1800-2200° C. to obtain the corresponding metal lattice doped reactor of the inner wall; the thickness of the active component film is formed on the inner wall of the reactor, i.e., the thickness is 10 nm-2 mm; then immediate cooling is conducted; and curing is made to obtain the reaction section of the catalytic reactor.

The metal salt used in the solid phase doping technology (the first method) is one or more than two of nitrate, soluble halogenide, soluble sulphate, soluble carbonate, soluble calcium phosphate, soluble organic alkoxide with C number of 1-2, or organic acid salt with C number of 1-2.

The metal salt used in the solid phase doping technology (the second method) is one or more than two of metal chloride, organic alkoxide of C number of 1-2, and organic acid salt of C number of 1-2.

The normal-temperature liquid metal chloride used in the solid phase doping technology (the third method) includes tin tetrachloride, titanium tetrachloride and germanium tetrachloride; and the normal-temperature liquid nonmetallic chloride or oxygen chloride includes boron trichloride and phosphorous oxychloride.

The preparation process of the solid phase doping technology (the first method) comprises an immersing process, and the solubility of immersion liquid is 50 ppm-5%; immersion time is 0.1-24 h, and preferably 1-18 h; and immersion temperature is preferably 20-80° C.

In the preparation process of the catalyst of the solid phase doping technology, deposition time is 10 min-2 h.

In the preparation process of the catalyst of the solid phase doping technology, the flow velocity of the support gas is 5-2000 ml/min.

The preparation process of the solid-liquid phase doping technology (sol-gel bonded with high temperature melting) comprises a sol-gel process, and the concentration of the metallic elements is 50 ppm-10%; the treatment time of sol is 2-100 h, and preferably 10-24 h; gel temperature is 10-120° C., and preferably 60-100° C.; and the treatment time of gel is 1-48 h, and preferably 2-10 h.

In the preparation process of the solid-liquid phase doping technology (sol-gel bonded with high temperature melting), the silicate comprises one or more than two of tetramethyl orthosilicate, tetraethoxysilane, tetrapropyl orthosilicate, isopropyl silicate, tetrabutyl orthosilicate or trimethylsiloxysilicate.

In the preparation process of the solid-liquid phase doping technology (sol-gel bonded with high temperature melting), the content ratio of the metal salt to the silicate is 1:1000 to 1:1, and the content ratio of the silicate to water is 1:0.1 to 1:10.

In the preparation process of the catalyst, a melting atmosphere is inert gas, air or oxygen; the inert gas comprises one or more of helium, argon or nitrogen; and melting time is 0.01-3 h.

In the preparation process of the catalyst, the thickness of the active component film is preferably 1 nm-0.05 mm, more preferably 1 nm-0.005 mm and further preferably 5 nm-50 nm.

The solidification is that the catalyst preparation process involves an important cooling process after the melting process; and the said cooling process includes rapid cooling or natural cooling.

The cooling is gas cooling. A cooling rate is preferably 50° C./s-2000° C./s, and preferably 100-1800° C./s; and the gas in the gas cooling is one or more than two of inert gases, nitrogen, oxygen or air.

The support gas is high purity oxygen or high purity helium (high purity refers to 99.999%).

The coated catalyst layer on the inner wall of the quartz or silica carbide reactor only comprises lattice doped metallic elements, and supports no metal or metal compound on the surface.

The catalysts that have dopant metal in amorphous-molten-state materials made from one or more than two of Si, C and O element can be expressed as A©SiO$_2$, A©SiC and A©SiC$_x$O$_y$ (4x+2y=4, and x and y are not zero at the same time), and the ranges of x and y are 0-1 and 0-2, and A denotes the dopant metallic elements.

The catalysts that have dopant non-metal in amorphous-molten-state materials made from one or more than two of Si, C and O element can be expressed as B©SiO$_2$ and B©SiC$_x$O$_y$ (4x+2y=4, and x and y are not zero at the same time), and the ranges of x and y are 0-1 and 0-2, and A denotes the dopant nonmetallic elements.

In A©SiO$_2$ metal doped catalysts, the metal element A is inserted in the lattice of SiO$_2$, and by partially replacing Si atoms, bonds with the adjacent O atoms (A-O). In A©SiC doped catalysts, the metal element A is inserted in the lattice of SiC, and by partially replacing Si or C atoms, bonds with the adjacent C or Si atoms (A-C or Si-A). In A©SiC$_x$O$_y$ doped catalysts, the metal element A is inserted the lattice of SiC$_x$O$_y$, and by partially replacing Si or C atoms, bonds with the adjacent C, O or Si atoms (A-C, A-O or A-Si).

In the B©SiO$_2$ doped catalysts, the nonmetallic element B is inserted in the lattice of SiO$_2$, and by partially replacing Si atoms, bonds with the adjacent O atoms (B—O). In the B©SiC$_x$O$_y$ doped catalysts, the metal element B is inserted the lattice of SiC$_x$O$_y$, and by partially replacing Si or C atoms, bonds with the adjacent C, O or Si atoms (B—C, B—O or B—Si).

The present invention relates to a synthesis method of ethylene from oxygen-free direct conversion of methane. Besides methane, the reaction feed gas includes possibly one or two of inert gases and non-inert gases. The inert gases include one or more than two of nitrogen, helium and argon, and the volume content of the inert gases in the reaction feed gas is 0-95%. The non-inert gases include one or a mixture of more than two of carbon monoxide, hydrogen, carbon dioxide, water, monohydric alcohol (with 2 to 4 carbon atoms) or alkanes with 2 to 4 carbon atoms, and the volume ratio of non-inert gases to the methane is 0-10%. The volume content of the methane in the reaction feed gas is 5-100%.

The present invention relates to a synthesis method of ethylene from oxygen-free direct conversion of methane. The reaction process includes a pretreatment process of a catalytic reactor, and the atmosphere of the pretreatment is reaction feed gas or hydrogen; pretreatment temperature is 750-900° C.; pretreatment pressure is 0.1-1 Mpa; and weight hourly space velocity of the reaction feed gas is 0.8-2.5 l/g/h, preferably 1.0-2.0 l/g/h.

The present invention relates to a synthesis method of ethylene from oxygen-free direct conversion of methane. The reaction process is in a continuous flow reaction mode. Under the continuous flow reaction mode, the reaction temperature is 800-1150° C.; the reaction pressure is preferably 0.1-0.5 MPa; and the weight hourly space velocity of the reaction feed gas is 1.0-30 L/g/h, preferably 4.0-20.0 L/g/h.

The present invention relates to a synthesis method of ethylene from oxygen-free direct conversion of methane, which also co-produces propylene, butylene, aromatics and hydrogen, and the aromatic hydrocarbon products include one or more of benzene, toluene, xylene, o-xylene, m-xylene, ethylbenzene, and naphthalene.

Based on the research of the methane dehydroaromatization process, the present invention proposes a metal lattice doped silicon-based catalyst for ethylene, aromatic hydrocarbon and hydrogen production by direct catalytic conversion of methane under oxygen-free reaction mode. Compared with the previous oxygen-free methane conversion process, especially with the patents with application numbers of 201310174960.5 and 201511003407.0, this method has the following characteristics:

| No. | 201310174960.5 201511003407.0 | The Invention |
|---|---|---|
| 1 | Reaction bed catalytic system, pressure drop of 0.1-0.5 MPa | No catalyst bed layer, and no pressure drop |
| 2 | Large radial temperature difference of reaction bed (about 50° C.) | No temperature difference |
| 3 | Methane conversion rate of 10-70% | Methane conversion rate of 20-90% |
| 4 | Catalyst life: less than 500 hours | Catalyst life: more than 1000 hours |
| 5 | Harsh preparation condition, and difficult scaleup of catalyst | No need of scaleup of catalyst |
| 6 | No similar industrial apparatus, and large design difficulty | Similar to the shell and tube reactor of ethane cracking and hydrocracking, and directly use it, and small industrialization difficulty |
| 7 | Oxidation reduction tolerant temperature (less than 1400° C.) | Oxidation reduction tolerant temperature (less than 1700° C.) |

Therefore, the method has the characteristics of high stability of catalyst, large conversion rate of methane, high selectivity of products, zero coke deposition, good process reproducibility, safe and reliable operation, etc., and has wide industrial application prospect.

Although it seems that there are some similarities in the product types between the process of the present invention and the existing methane dehydroaromatization, the study finds that there are fundamental differences (in catalysts and reaction mechanism). Firstly, the methane dehydroaromatization catalyst is a zeolite supported catalyst. Secondly, the current accepted reaction mechanism for methane dehydroaromatization (shown in Formula 1) is: methane is dissociated on the surface of the resulting active sites (such as $MoC_x$, WC, Re) of the catalyst to produce $CH_x$ species; subsequently, $CH_x$ species are coupled on the surface of catalyst to form the $C_2H_y$ species; then $C_2H_y$ species are coupled on the acidic sites of the zeolite channel, in which aromatic hydrocarbon is formed by the shape selectivity of zeolite channel. (J. Energy Chem. 2013, 22, 1-20).

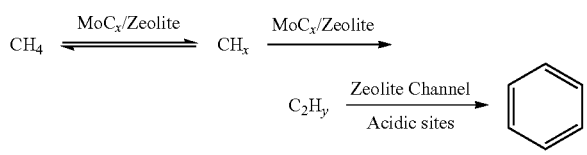

Formula 1: Reaction Mechanism of the Methane Dehydroaromatization Over $MoC_x$/Zeolite Catalyst.

However, the catalysts of the present invention are amorphous molten materials formed by lattice-doping the metal elements in one or more than two of Si, C and O. The reaction mechanism is that methane is induced by the active species (combined metallic elements in the lattice) to produce $CH_3$ radicals, which are further coupled and dehydrogened to obtain the olefins, aromatic hydrocarbon and hydrogen (as shown in Formula 2).

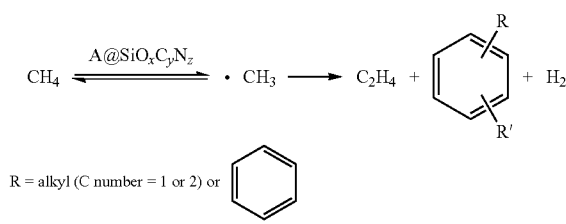

R = alkyl (C number = 1 or 2) or

R' = alkyl (C number = 0 or 1)

Formula 2 Radical Mechanism of Oxygen-Free Production of Alkene from Catalysis of Methane by $A@SiO_xC_yN_z$ Catalyst The differences between the methane dehydroaromatization and the present invention are as follows: 1) it is necessary for the methane dehydroaromatization to possess zeolite with specific channel size and structure, as well as acidic sites with certain amount and types; 2) the catalysts in the present invention are amorphous molten state materials without channel and acid; 3) the mechanism of methane dehydroaromatization is a synergistic catalysis mechanism between active species and zeolite (channel and acidic), while the present invention is a radical induction mechanism.

In the present invention, the methane conversion is 20-90%; ethylene selectivity is 65-95%; propylene and butylene selectivities are 5-10%; aromatic hydrocarbon selectivity is 0-30%; and zero coke deposition. The method has the characteristics of long life of catalysts (>1000 h), high stability of redox and hydrothermal conditions at high temperature (<1700° C.), high conversion rate of methane, high selectivity of ethylene, zero coke deposition, easy separation of products, no scaleup of catalyst, small industrialization difficulty, good process reproducibility, safe and reliable operation and the like, and has wide industrial application prospect.

DESCRIPTION OF PREFERRED EMBODIMENTS

The present invention is described below in details in combination with the drawings and the specific embodiments. However, the following embodiments are limited to explaining the present invention. The protection scope of the present invention should include all contents of claims, not limited to the embodiments.

Figure 2:
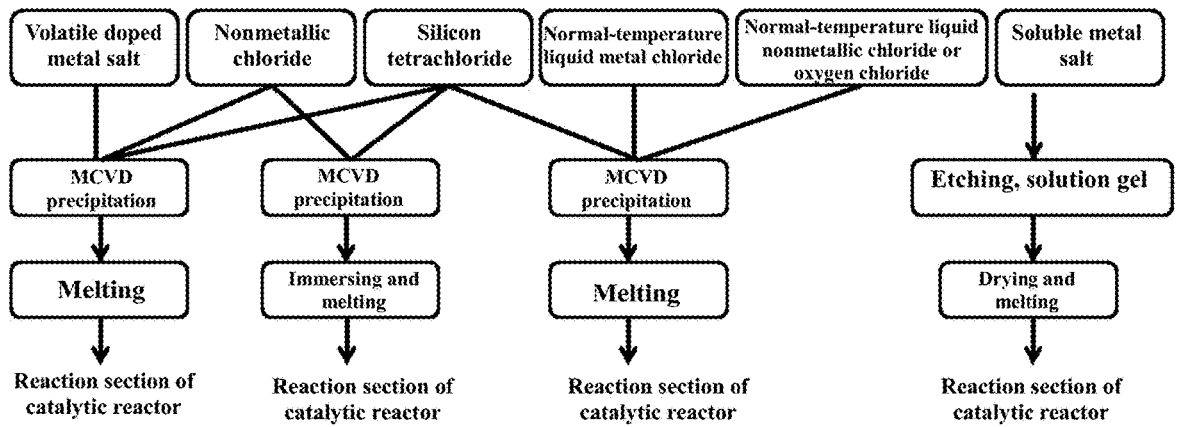
FIG. 2 is a process diagram of a preparation method of the present invention.

As shown in FIG. 2, the preparation method of the present invention is specifically realized as follows:

1. Preparation of Reaction Section of Catalytic Reactor

The preparation methods of the lattice doped catalyst include a modified chemical vapor deposition (MCVD) coated solid phase doping technology or a solid-liquid phase sol-gel combined high temperature melting and coating technology. The catalyst of the film is marked as A©SiO$_x$C$_y$.

The preparation of A©SiO$_2$ lattice doped catalysts (embodiments 1-20); the preparation of A©SiC lattice doped catalysts (embodiments 21-26); the preparation of A©SiOC$_{0.5}$ all lattice doped catalysts (embodiments 27-30); the preparation of A/SiO$_2$ support type catalysts (embodiment 31) (Active components are dispersed on the support surface); the preparation of A@SiO$_2$ partial lattice doped catalysts (embodiments 32-34) (Active components are partially dispersed on the support surface, and a part of lattice is doped in the support, such as patent 201310174960.5).

Embodiment 1

Modified Chemical Vapor Deposition (MCVD)

SiCl$_4$ liquid and FeCl$_3$ gas of 350° C. are brought into high temperature MCVD by using 30 mL/min of high purity oxygen; at 1600° C., SiCl$_4$ and FeCl$_3$ conduct oxidation deposition on the inner wall of a quartz tube (with a wall thickness of 1.5 mm) with an outer diameter of 20 mm and a length of 100 mm for 10 minutes to obtain Fe doped SiO$_2$ powder material; subsequently, under a temperature of 1980° C. and 2 bars of highly pure helium atmosphere, the material is melted for 40 minutes; then, a dopant thin layer with a thickness of 50 nm is formed on the inner wall of the reaction section; and the material is cooled naturally to obtain the reaction section A of a Fe© catalytic quartz reactor with a diameter of 20 mm and a length of 100 mm, wherein the doping amount of Fe is 0.35 wt. %.

Embodiment 2

Modified Chemical Vapor Deposition (MCVD)

SiCl$_4$ liquid and FeCl$_3$ gas of 350° C. are brought into high temperature MCVD by using 30 mL/min of high purity helium; at 1650° C., SiCl$_4$ and FeCl$_3$ conduct high purity oxygen reaction on the inner wall of a quartz tube with an outer diameter of 20 mm (with a wall thickness of 1.5 mm) and a length of 150 mm for oxidization deposition for 30 minutes to obtain Fe doped SiO$_2$ powder material; subsequently, under a temperature of 1980° C. and 2 bars of highly pure argon atmosphere, the material is melted for 40 minutes; then, a dopant thin layer with a thickness of 50 nm is formed on the inner wall of the reaction section; and the material is cooled naturally to obtain the reaction section B of a Fe© catalytic quartz reactor with a diameter of 20 mm and a length of 150 mm, wherein the doping amount of Fe is 0.6 wt. %.

Embodiment 3

Modified Chemical Vapor Deposition (MCVD)

SiCl$_4$ liquid and ZnCl$_2$ gas of 750° C. are brought into high temperature MCVD by using 30 mL/min of high purity oxygen; at 1600° C., SiCl$_4$ and ZnCl$_2$ conduct oxidization deposition on the inner wall of a quartz tube with an outer diameter of 20 mm (with a wall thickness of 1.5 mm) and a length of 200 mm for 30 minutes to obtain Zn doped SiO$_2$ powder material; subsequently, under a temperature of 2000° C. and 1.5 bars of highly pure helium atmosphere, the material is melted for 40 minutes; then, a dopant thin layer with a thickness of 50 nm is formed on the inner wall of the reaction section; and the material is cooled naturally to obtain the reaction section C of a Zn© catalytic quartz reactor with a diameter of 20 mm and a length of 200 mm, wherein the doping amount of Zn is 0.55 wt. %.

Embodiment 4

Modified Chemical Vapor Deposition (MCVD)

SiCl$_4$ liquid, FeCl$_3$ gas of 350° C., and ZnCl$_2$ gas of 750° C. are brought into high temperature MCVD by using 30 mL/min of high purity helium; at 1600° C., SiCl$_4$, FeCl$_3$, and ZnCl$_2$ react with highly pure oxygen to conduct oxidization deposition on the inner wall of a quartz tube with an outer diameter of 20 mm (with a wall thickness of 1.5 mm) and a length of 280 mm for 30 minutes to obtain SiO$_2$ powder material doped with Fe and Zn; subsequently, under a temperature of 2000° C. and 1.5 bars of highly pure argon atmosphere, the material is melted for 40 minutes; then, a dopant thin layer with a thickness of 100 nm is formed on the inner wall of the reaction section; and the material is cooled naturally to obtain the reaction section D of a Fe—Zn—P© catalytic quartz reactor with a diameter of 20 mm and a length of 280 mm, wherein the doping amounts of Fe and Zn are respectively 0.6 wt. % and 0.55 wt. %.

Embodiment 5

Modified Chemical Vapor Deposition (MCVD)

SiCl$_4$ liquid, FeCl$_3$ gas of 350° C., and ZnCl$_2$ gas of 750° C. are brought into high temperature MCVD by using 30 mL/min of high purity oxygen; at 1600° C., SiCl$_4$, FeCl$_3$, and ZnCl$_2$ conduct oxidization deposition on the inner wall of a quartz tube with an outer diameter of 50 mm (with a wall thickness of 2 mm) and a length of 350 mm for 60 minutes to obtain SiO$_2$ powder material doped with Fe and Zn; subsequently, under a temperature of 2000° C. and 1.5 bars of highly pure argon atmosphere, the material is melted for 60 minutes; then, a dopant thin layer with a thickness of 100 nm is formed on the inner wall of the reaction section; and the material is cooled naturally to obtain the reaction section E of a Fe—Zn© catalytic quartz reactor with a diameter of 50 mm and a length of 350 mm, wherein the doping amounts of Fe and Zn are respectively 0.8 wt. % and 0.65 wt. %.

Embodiment 6

Modified Chemical Vapor Deposition (MCVD)

SiCl$_4$ liquid, FeCl$_3$ gas of 350° C., ZnCl$_2$ gas of 750° C. and POCl$_3$ liquid are brought into high temperature MCVD by using 30 mL/min of high purity oxygen; at 1600° C., SiCl$_4$, FeCl$_3$, ZnCl$_2$ and POCl$_3$ conduct oxidization deposition on the inner wall of a quartz tube with an outer diameter of 20 mm (with a wall thickness of 1.5 mm) and a length of 300 mm for 45 minutes to obtain $SiO_2$ powder material doped with Fe, Zn and P; subsequently, under a temperature of 2000° C. and 1.5 bars of pure argon atmosphere, the material is melted for 40 minutes; then, a dopant thin layer with a thickness of 80 nm is formed on the inner wall of the reaction section; and the material is cooled naturally to obtain the reaction section F of a Fe—Zn—P© catalytic quartz reactor with a diameter of 20 mm and a length of 300 mm, wherein the doping amounts of Fe, Zn and P are respectively 0.7 wt. %, 0.6 wt. % and 0.8 wt. %.

Embodiment 7

Modified Chemical Vapor Deposition (MCVD)

$SiCl_4$ liquid, $SnCl_4$ liquid, $ZnCl_2$ gas of 750° C. and $POCl_3$ liquid are brought into high temperature MCVD by using 30 mL/min of high purity oxygen; at 1600° C., $SiCl_4$, $SnCl_4$, $ZnCl_2$ and $POCl_3$ conduct oxidization deposition on the inner wall of a quartz tube with an outer diameter of 20 mm (with a wall thickness of 1.5 mm) and a length of 250 mm for 45 minutes to obtain $SiO_2$ powder material doped with Sn, Zn and P; subsequently, under a temperature of 2000° C. and 1.5 bars of pure argon atmosphere, the material is melted for 40 minutes; then, a dopant thin layer with a thickness of 80 nm is formed on the inner wall of the reaction section; and the material is cooled naturally to obtain the reaction section G of a Fe—Zn—P© catalytic quartz reactor with a diameter of 20 mm and a length of 250 mm, wherein the doping amounts of Sn, Zn and P are respectively 0.4 wt. %, 0.6 wt. % and 0.8 wt. %.

Embodiment 8

Modified Chemical Vapor Deposition (MCVD)

$SiCl_4$ liquid, $SnCl_4$ liquid, $ZnCl_2$ gas of 750° C. and $POCl_3$ liquid are brought into high temperature MCVD by using 30 mL/min of high purity helium; at 1600° C., $SiCl_4$, $SnCl_4$, $ZnCl_2$ and $POCl_3$ react with the high purity oxygen to conduct oxidization deposition on the inner wall of a quartz tube with an outer diameter of 20 mm (with a wall thickness of 1.5 mm) and a length of 150 mm for 45 minutes to obtain $SiO_2$ powder material doped with Sn, Zn and P; subsequently, under a temperature of 2000° C. and 1.5 bars of high purity oxygen atmosphere, the material is melted for 40 minutes; then, a dopant thin layer with a thickness of 85 nm is formed on the inner wall of the reaction section; and the material is cooled naturally to obtain the reaction section H of a Sn—Zn—P© catalytic quartz reactor with a diameter of 20 mm and a length of 150 mm, wherein the doping amounts of Sn, Zn and P are respectively 0.4 wt. %, 0.6 wt. % and 0.8 wt. %.

Embodiment 9

Modified Chemical Vapor Deposition (MCVD)

$SiCl_4$ liquid, $TiCl_4$ liquid, $FeCl_3$ gas of 320° C. and $BCl_3$ liquid are brought into high temperature MCVD by using 30 mL/min of high purity oxygen; at 1600° C., $SiCl_4$, $TiCl_4$, $FeCl_3$ and $BCl_3$ conduct oxidization deposition on the inner wall of a quartz tube with an outer diameter of 20 mm (with a wall thickness of 1.5 mm) and a length of 600 mm for 45 minutes to obtain $SiO_2$ powder material doped with Ti, Fe and B; subsequently, under a temperature of 2000° C. and 1.5 bars of pure helium atmosphere, the material is melted for 40 minutes; then, a dopant thin layer with a thickness of 40 nm is formed on the inner wall of the reaction section; and the material is cooled naturally to obtain the reaction section I of a Ti—Fe—B© catalytic quartz reactor with a diameter of 20 mm and a length of 600 mm, wherein the doping amounts of Ti, Fe and B are respectively 0.5 wt. %, 0.4 wt. % and 0.6 wt. %.

Embodiment 10

Modified Chemical Vapor Deposition (MCVD)

$SiCl_4$ liquid, $GaCl_3$ liquid of 220° C., and $AlCl_3$ gas of 180° C. are brought into high temperature MCVD by using 30 mL/min of high purity helium; at 1650° C., $SiCl_4$, $GaCl_3$, and $AlCl_3$ react with highly pure oxygen to conduct oxidization deposition on the inner wall of a quartz tube with an outer diameter of 20 mm (with a wall thickness of 1.5 mm) and a length of 250 mm for 40 minutes to obtain $SiO_2$ powder material doped with Ga and Al; subsequently, under a temperature of 2000° C. and 1.5 bars of highly pure argon atmosphere, the material is melted for 40 minutes; then, a dopant thin layer with a thickness of 60 nm is formed on the inner wall of the reaction section; and the material is cooled naturally to obtain the reaction section J of a Ga—Al© catalytic quartz reactor with a diameter of 20 mm and a length of 250 mm, wherein the doping amounts of Ga and Al are respectively 0.5 wt. % and 0.6 wt. %.

Embodiment 11

Modified Chemical Vapor Deposition (MCVD)

$SiCl_4$ liquid, $YbCl_3$ liquid of 900° C., $AlCl_3$ gas of 180° C. and $POCl_3$ liquid are brought into high temperature MCVD by using 30 mL/min of high purity helium; at 1650° C., $SiCl_4$, $YbCl_3$, $POCl_3$ and $AlCl_3$ react with highly pure oxygen to conduct oxidization deposition on the inner wall of a quartz tube with an outer diameter of 20 mm (with a wall thickness of 1.5 mm) and a length of 100 mm for 40 minutes to obtain $SiO_2$ powder material doped with Yb and Al; subsequently, under a temperature of 2000° C. and 1.5 bars of high purity oxygen atmosphere, the material is melted for 40 minutes; then, a dopant thin layer with a thickness of 80 nm is formed on the inner wall of the reaction section; and the material is cooled naturally to obtain the reaction section K of a Yb—Al—P© catalytic quartz reactor with a diameter of 20 mm and a length of 100 mm, wherein the doping amounts of Yb, Al and P are respectively 0.2 wt. %, 0.5 wt. % and 0.6 wt. %.

Embodiment 12

Modified Chemical Vapor Deposition (MCVD)

$SiCl_4$ liquid, $LaCl_3$ liquid of 900° C., $AlCl_3$ gas of 180° C. and $BCl_3$ liquid are brought into high temperature MCVD by using 30 mL/min of high purity oxygen; at 1650° C., $SiCl_4$, $LaCl_3$, $BCl_3$ and $AlCl_3$ conduct oxidization deposition on the inner wall of a quartz tube with an outer diameter of 50 mm (with a wall thickness of 2 mm) and a length of 1500 mm for 80 minutes to obtain $SiO_2$ powder material doped with La, Al and B; subsequently, under a temperature of 2000° C. and 1.5 bars of high purity helium atmosphere, the material is melted for 60 minutes; then, a dopant thin layer with a thickness of 150 nm is formed on the inner wall of the reaction section; and the material is cooled naturally to obtain the reaction section L of a La—Al—B© catalytic quartz reactor with a diameter of 50 mm and a length of 1500 mm, wherein the doping amounts of La, Al and B are respectively 0.2 wt. %, 0.4 wt. % and 0.6 wt. %.

Embodiment 13

Modified Chemical Vapor Deposition (MCVD)

$SiCl_4$ liquid, $LaCl_3$ liquid of 900° C., $AlCl_3$ gas of 180° C. and $BCl_3$ liquid are brought into high temperature MCVD by using 30 mL/min of high purity helium; at 1650° C., $SiCl_4$, $LaCl_3$, $BCl_3$ and $AlCl_3$ conduct oxidization deposition on the inner wall of a quartz tube with an outer diameter of 50 mm (with a wall thickness of 2 mm) and a length of 1200 mm for 80 minutes to obtain $SiO_2$ powder material doped with La, Al and B; subsequently, under a temperature of 2000° C. and 1.5 bars of high purity argon atmosphere, the material is melted for 60 minutes; then, a dopant thin layer with a thickness of 150 nm is formed on the inner wall of the reaction section; and the material is cooled naturally to obtain the reaction section M of a La—Al—B© catalytic quartz reactor with a diameter of 50 mm and a length of 1200 mm, wherein the doping amounts of La, Al and B are respectively 0.2 wt. %, 0.4 wt. % and 0.6 wt. %.

Embodiment 14

Modified Chemical Vapor Deposition (MCVD)

$SiCl_4$ liquid, $BCl_3$ liquid, and $POCl_3$ liquid are brought into high temperature MCVD by using 30 mL/min of high purity oxygen; at 1650° C., $SiCl_4$, $BCl_3$, and $POCl_3$ conduct oxidization deposition on the inner wall of a quartz tube with an outer diameter of 25 mm (with a wall thickness of 1.5 mm) and a length of 250 mm for 30 minutes to obtain $SiO_2$ powder material doped with B and P; subsequently, under a temperature of 2000° C. and 1.5 bars of highly pure helium atmosphere, the material is melted for 40 minutes; then, a dopant thin layer with a thickness of 50 nm is formed on the inner wall of the reaction section; and the material is cooled naturally to obtain the reaction section N of a P—B© catalytic quartz reactor with a diameter of 25 mm and a length of 250 mm, wherein the doping amounts of P and B are respectively 0.6 wt. % and 0.5 wt. %.

Embodiment 15

Modified Chemical Vapor Deposition (MCVD)

$SiCl_4$ liquid, $MgCl_2$ liquid of 950° C., $MnCl_2$ liquid of 950° C. and $POCl_3$ liquid are brought into high temperature MCVD by using 30 mL/min of high purity oxygen; at 1650° C., $SiCl_4$, $MgCl_2$, $MnCl_2$ and $POCl_3$ conduct oxidization deposition on the inner wall of a quartz tube with an outer diameter of 30 mm (with a wall thickness of 1.5 mm) and a length of 200 mm for 40 minutes to obtain $SiO_2$ powder material doped with Mg, Mn and P; subsequently, under a temperature of 2000° C. and 1.5 bars of highly pure helium atmosphere, the material is melted for 40 minutes; then, a dopant thin layer with a thickness of 70 nm is formed on the inner wall of the reaction section; and the material is cooled naturally to obtain the reaction section 0 of a Mg—Mn—P© catalytic quartz reactor with a diameter of 30 mm and a length of 200 mm, wherein the doping amounts of Mg, Mn and P are respectively 0.6 wt. %, 0.5 wt. % and 0.7 wt. %.

Embodiment 16

Modified Chemical Vapor Deposition (MCVD)

$SiCl_4$ liquid, $MgCl_2$ liquid of 950° C., $MnCl_2$ liquid of 950° C. and $POCl_3$ liquid are brought into high temperature MCVD by using 30 mL/min of high purity oxygen; at 1650° C., $SiCl_4$, $MgCl_2$, $MnCl_2$ and $POCl_3$ conduct oxidization deposition on the inner wall of a quartz tube with an outer diameter of 30 mm (with a wall thickness of 1.5 mm) and a length of 900 mm for 40 minutes to obtain $SiO_2$ powder material doped with Mg, Mn and P; subsequently, under a temperature of 2000° C. and 1.5 bars of pure oxygen atmosphere, the material is melted for 40 minutes; then, a dopant thin layer with a thickness of 70 nm is formed on the inner wall of the reaction section; and the material is cooled naturally to obtain the reaction section P of a Mg—Mn—P© catalytic quartz reactor with a diameter of 30 mm and a length of 900 mm, wherein the doping amounts of Mg, Mn and P are respectively 0.4 wt. %, 0.3 wt. % and 0.4 wt. %.

Embodiment 17

Modified Chemical Vapor Deposition (MCVD)

$SiCl_4$ liquid, $FeCl_3$ gas of 350° C., $MnCl_2$ liquid of 950° C., $POCl_3$ liquid, $AlCl_3$ gas of 180° C. and $SnCl_4$ liquid are brought into high temperature MCVD by using 30 mL/min of high purity oxygen; at 1650° C., $SiCl_4$, $FeCl_3$, $MnCl_2$, $AlCl_3$, $SnCl_4$ and $POCl_3$ conduct oxidization deposition on the inner wall of a quartz tube with an outer diameter of 20 mm (with a wall thickness of 1.5 mm) and a length of 800 mm for 60 minutes to obtain $SiO_2$ powder material doped with Fe, Mn, Sn, Al and P; subsequently, under a temperature of 2050° C. and 1.5 bars of pure oxygen atmosphere, the material is melted for 60 minutes; then, a dopant thin layer with a thickness of 100 nm is formed on the inner wall of the reaction section; and the material is cooled naturally to obtain the reaction section Q of a Fe—Mn—Sn—Al—P© catalytic reactor with a diameter of 20 mm and a length of 800 mm, wherein the doping amounts of Fe, Mn, Sn, Al and P are respectively 0.4 wt. %, 0.3 wt. %, 0.2 wt. %, 0.45 wt. % and 0.4 wt. %.

Embodiment 18

Modified Chemical Vapor Deposition (MCVD)

$SiCl_4$ liquid is brought into high temperature MCVD by using 30 mL/min of high purity oxygen; at 1650° C., $SiCl_4$ conducts oxidation deposition on the inner wall of a quartz tube with an outer diameter of 20 mm (with a wall thickness of 1.5 mm) and a length of 500 mm for 40 minutes to obtain $SiO_2$ powder material; subsequently, under a temperature of 50° C., the quartz tube of 20 mm is immersed in an aqueous solution of $SrCl_2$ and $Ba(NO_3)_2$ to for about 2 h; subsequently, under a temperature of 2000° C. and 1.5 bars of pure argon atmosphere, the material is melted for 40 minutes; then, a dopant thin layer with a thickness of 300 nm is formed on the inner wall of the reaction section; and the material is cooled naturally to obtain the reaction section R of a Sr—Ba© catalytic quartz reactor with a diameter of 20 mm and a length of 500 mm, wherein the doping amounts of Sr and Ba are respectively 0.4 wt. % and 0.4 wt. %.

Embodiment 19

Modified Chemical Vapor Deposition (MCVD)

$SiCl_4$ liquid, $LaCl_3$ liquid of 900° C., $AlCl_3$ gas of 180° C. and $BCl_3$ liquid are brought into high temperature MCVD by using 30 mL/min of high purity oxygen; at 1650° C., $SiCl_4$, $LaCl_3$, $BCl_3$ and $AlCl_3$ conduct oxidation deposition on the inner wall of a quartz tube with an outer diameter of 50 mm (with a wall thickness of 2 mm) and a length of 200 mm for 80 minutes to obtain $SiO_2$ powder material doped with La, Al and B; subsequently, under a temperature of 50° C., the quartz reactor of 50 mm is immersed in an aqueous solution of $AuCl_3$ to for about 1 h; subsequently, under a temperature of 2000° C. and 1.5 bars of pure oxygen atmosphere, the material is melted for 60 minutes; then, a dopant thin layer with a thickness of 100 nm is formed on the inner wall of the reaction section; and the material is cooled naturally to obtain the reaction section S of a La—Al—Au—B© catalytic quartz reactor with a diameter of 50 mm and a length of 200 mm, wherein the doping amounts of La, Al, Au and B are respectively 0.4 wt. %, 0.5 wt. %, 0.1 wt. % and 0.4 wt. %.

Embodiment 20

Modified Chemical Vapor Deposition (MCVD)

$SiCl_4$ liquid, $LaCl_3$ liquid of 900° C., $AlCl_3$ gas of 180° C. and $BCl_3$ liquid are brought into high temperature MCVD by using 30 mL/min of high purity oxygen; at 1650° C., $SiCl_4$, $LaCl_3$, $BCl_3$ and $AlCl_3$ conduct oxidation deposition on the inner wall of a quartz tube with an outer diameter of 50 mm (with a wall thickness of 2 mm) and a length of 300 mm for 80 minutes to obtain $SiO_2$ powder material doped with La, Al and B; subsequently, under a temperature of 50° C., the quartz reactor of 50 mm is immersed in an aqueous solution of $AuCl_3$ to for about 1 h; subsequently, under a temperature of 2000° C. and 1.5 bars of pure oxygen atmosphere, the material is melted for 60 minutes; then, a dopant thin layer with a thickness of 80 nm is formed on the inner wall of the reaction section; and the material is cooled naturally to obtain the reaction section T of a La—Al—Au—B© catalytic quartz reactor with a diameter of 50 mm and a length of 300 mm, wherein the doping amounts of La, Al, Au and B are respectively 0.3 wt. %, 0.5 wt. %, 0.2 wt. % and 0.5 wt. %.

Embodiment 21

Modified Chemical Vapor Deposition (MCVD)

$SiCl_4$ liquid, $FeCl_3$ gas of 350° C., $ZnCl_2$ gas of 750° C. and $POCl_3$ liquid are brought into high temperature MCVD by using 30 mL/min of high purity oxygen; at 1650° C., $SiCl_4$, $FeCl_3$, $ZnCl_2$ and $POCl_3$ conduct oxidization deposition on the inner wall of a quartz tube with an outer diameter of 40 mm (with a wall thickness of 2 mm) and a length of 300 mm for 60 minutes to obtain $SiO_2$ powder material doped with Fe, Zn and P; subsequently, under a temperature of 2000° C. and 1.5 bars of pure argon atmosphere, the material is melted for 40 minutes; then, a dopant thin layer with a thickness of 80 nm is formed on the inner wall of the reaction section; and the material is cooled naturally to obtain the reaction section U of a Fe—Zn—P© catalytic quartz reactor with a diameter of 40 mm and a length of 300 mm, wherein the doping amounts of Fe, Zn and P are respectively 0.6 wt. %, 0.5 wt. % and 0.35 wt. %.

Embodiment 22

Modified Chemical Vapor Deposition (MCVD)

$SiCl_4$ liquid, $FeCl_3$ gas of 350° C., $ZnCl_2$ gas of 750° C. and $POCl_3$ liquid are brought into high temperature MCVD by using 30 mL/min of high purity oxygen; at 1650° C., $SiCl_4$, $FeCl_3$, $ZnCl_2$ and $POCl_3$ conduct oxidization deposition on the inner wall of a silica carbide tube with an outer diameter of 20 mm (with a wall thickness of 2.5 mm) and a length of 400 mm for 60 minutes to obtain $SiO_2$ powder material doped with Fe, Zn and P; subsequently, under a temperature of 1650° C., $CH_4$ is led to conduct carbonizing treatment for 60 minutes; subsequently, under a temperature of 2000° C. and 1.5 bars of pure argon atmosphere, the material is melted for 40 minutes; then, a dopant thin layer with a thickness of 120 nm is formed on the inner wall of the reaction section; and the material is cooled naturally to obtain the reaction section V of a Fe—Zn—P© catalytic silica carbide reactor with a diameter of 20 mm and a length of 400 mm, wherein the doping amounts of Fe, Zn and P are respectively 0.2 wt. %, 0.3 wt. % and 0.5 wt. %.

Embodiment 23

Modified Chemical Vapor Deposition (MCVD)

$SiCl_4$ liquid, $FeCl_3$ gas of 350° C., $ZnCl_2$ gas of 750° C. and $POCl_3$ liquid are brought into high temperature MCVD by using 30 mL/min of high purity oxygen; at 1650° C., $SiCl_4$, $FeCl_3$, $ZnCl_2$ and $POCl_3$ conduct oxidization deposition on the inner wall of a silica carbide tube with an outer diameter of 20 mm (with a wall thickness of 2.5 mm) and a length of 600 mm for 60 minutes to obtain $SiO_2$ powder material doped with Fe, Zn and P; subsequently, under a temperature of 1650° C., $CH_4$ is led at 60 ml/min to conduct carbonizing treatment for 60 minutes; subsequently, under a temperature of 2000° C. and 1.5 bars of pure argon atmosphere, the material is melted for 40 minutes; then, a dopant thin layer with a thickness of 800 nm is formed on the inner wall of the reaction section; and the material is cooled naturally to obtain the reaction section W of a Fe—Zn—P© catalytic silica carbide reactor with a diameter of 20 mm and a length of 600 mm, wherein the doping amounts of Fe, Zn and P are respectively 0.3 wt. %, 0.2 wt. % and 0.4 wt. %.

Embodiment 24

Modified Chemical Vapor Deposition (MCVD)

$SiCl_4$ liquid, $FeCl_3$ gas of 350° C., $ZnCl_2$ gas of 750° C. and $POCl_3$ liquid are brought into high temperature MCVD by using 30 mL/min of high purity oxygen; at 1650° C., $SiCl_4$, $FeCl_3$, $ZnCl_2$ and $POCl_3$ conduct oxidization deposition on the inner wall of a silica carbide tube with an outer diameter of 20 mm (with a wall thickness of 2.5 mm) and a length of 360 mm for 80 minutes to obtain $SiO_2$ powder material doped with Fe, Zn and P; subsequently, under a temperature of 1650° C., $CH_4$ is led at 40 ml/min to conduct carbonizing treatment for 60 minutes; subsequently, under a temperature of 2000° C. and 1.5 bars of pure argon atmosphere, the material is melted for 60 minutes; then, a dopant thin layer with a thickness of 600 nm is formed on the inner wall of the reaction section; and the material is cooled naturally to obtain the reaction section X of a Fe—Zn—P© catalytic silica carbide reactor with a diameter of 50 mm and a length of 360 mm, wherein the doping amounts of Fe, Zn and P are respectively 0.4 wt. %, 0.3 wt. % and 0.2 wt. %.

Embodiment 25

Modified Chemical Vapor Deposition (MCVD)

$SiCl_4$ liquid, $FeCl_3$ gas of 350° C., $ZnCl_2$ gas of 750° C. and $POCl_3$ liquid are brought into high temperature MCVD by using 30 mL/min of high purity oxygen; at 1650° C., $SiCl_4$, $FeCl_3$, $ZnCl_2$ and $POCl_3$ conduct oxidization deposition on the inner wall of a silica carbide tube with an outer diameter of 20 mm (with a wall thickness of 2 mm) and a length of 600 mm for 40 minutes to obtain $SiO_2$ powder material doped with Fe, Zn and P; subsequently, under a temperature of 2000° C. and 1.5 bars of pure argon atmosphere, the material is melted for 60 minutes; then, a dopant thin layer with a thickness of 500 nm is formed on the inner wall of the reaction section; and the material is cooled naturally to obtain the $SiO_2$ coated reaction section Y of a Fe—Zn—P© catalytic silica carbide reactor with a diameter of 20 mm and a length of 600 mm, wherein the doping amounts of Fe, Zn and P are respectively 0.3 wt. %, 0.2 wt. % and 0.2 wt. %.

Embodiment 26

Modified Chemical Vapor Deposition (MCVD)

$SiCl_4$ liquid, $FeCl_3$ gas of 350° C., $ZnCl_2$ gas of 750° C. and $POCl_3$ liquid are brought into high temperature MCVD by using 30 mL/min of high purity oxygen; at 1650° C., $SiCl_4$, $FeCl_3$, $ZnCl_2$ and $POCl_3$ conduct oxidization deposition on the inner wall of a silica carbide tube with an outer diameter of 50 mm (with a wall thickness of 3 mm) and a length of 400 mm for 80 minutes to obtain $SiO_2$ powder material doped with Fe, Zn and P; subsequently, under a temperature of 2000° C. and 1.5 bars of pure argon atmosphere, the material is melted for 60 minutes; then, a dopant thin layer with a thickness of 300 nm is formed on the inner wall of the reaction section; and the material is cooled naturally to obtain the $SiO_2$ coated reaction section Z of a Fe—Zn—P© catalytic silica carbide reactor with a diameter of 50 mm and a length of 400 mm, wherein the doping amounts of Fe, Zn and P are respectively 0.1 wt. %, 0.4 wt. % and 0.35 wt. %.

Embodiment 27

A sol-gel method is combined with a high temperature melting technology.

The inner wall of the quartz tube with an outer diameter of 13 mm is treated for 2 h by using 20% of HF solution; meanwhile, a mixed solution of 0.3688 g of $Fe(NO_3)_3.9H_2O$, 33 mL of tetraethoxysilane TEOS and 50 mL of deionized water is prepared; after uniformly stirred, 4 mL is taken and coated on the HF etched inner wall of the quartz tube; subsequently, treatment is made in an oven under a temperature of 90° C. for 3 h; finally, under a temperature of 2050° C. and normal pressure air atmosphere, the material is melted for 60 minutes; then, a dopant thin layer with a thickness of 90 nm is formed on the inner wall of the reaction section; and the material is cooled naturally to obtain the reaction section AA of a Fe© catalytic quartz reactor with a diameter of 13 mm and a length of 100 mm, wherein the doping amount of Fe is 0.5 wt. %.

Embodiment 28

A sol-gel method is combined with a high temperature melting technology.

The inner wall of the quartz tube with an outer diameter of 16 mm and a length of 400 mm is treated for 2 h by using 20% of HF solution; meanwhile, a mixed solution of 0.5344 g of $Mg(NO_3)_2.6H_2O$, 33 mL of tetraethoxysilane TEOS and 50 mL of deionized water is prepared; after uniformly stirred, 6 mL is taken and coated on the HF etched inner wall of the quartz tube; subsequently, treatment is made in an oven under a temperature of 90° C. for 3 h; finally, under a temperature of 1950° C. and normal pressure air atmosphere, the material is melted for 60 minutes; then, a dopant thin layer with a thickness of 120 nm is formed on the inner wall of the reaction section; and the material is cooled naturally to obtain the reaction section AB of a Mg© catalytic quartz reactor with a diameter of 16 mm and a length of 400 mm, wherein the doping amount of Mg is 0.6 wt. %.

Embodiment 29

A sol-gel method is combined with a high temperature melting technology.

The inner wall of the quartz tube with an outer diameter of 20 mm and a length of 200 mm is treated for 2 h by using 20% of HF solution; meanwhile, a mixed solution of 0.2288 g of $Zn(NO_3)_2.6H_2O$, 33 mL of tetraethoxysilane TEOS and 50 mL of deionized water is prepared; after uniformly stirred, 4 mL is taken and coated on the HF etched inner wall of the quartz tube; subsequently, treatment is made in an oven under a temperature of 90° C. for 3 h; finally, under a temperature of 2000° C. and normal pressure air atmosphere, the material is melted for 40 minutes; then, a dopant thin layer with a thickness of 200 nm is formed on the inner wall of the reaction section; and the material is cooled naturally to obtain the reaction section AC of a Zn© catalytic quartz reactor with a diameter of 20 mm and a length of 200 mm, wherein the doping amount of Zn is 0.5 wt. %.

Embodiment 30

A sol-gel method is combined with a high temperature melting technology.

The inner wall of the quartz tube with an outer diameter of 20 mm and a length of 250 mm is treated for 2 h by using 20% of HF solution; meanwhile, a mixed solution of 0.1559 of $La(NO_3)_2.6H_2O$, 33 mL of tetraethoxysilane TEOS and 50 mL of deionized water is prepared; after uniformly stirred, 4 mL is taken and coated on the HF etched inner wall of the quartz tube; subsequently, treatment is made in an oven under a temperature of 90° C. for 3 h; finally, under a temperature of 2000° C. and normal pressure air atmosphere, the material is melted for 40 minutes; then, a dopant thin layer with a thickness of 150 nm is formed on the inner wall of the reaction section; and the material is cooled naturally to obtain the reaction section AD of a La© catalytic quartz reactor with a diameter of 20 mm and a length of 250 mm, wherein the doping amount of La is 0.6 wt. %.

Embodiment 31

A sol-gel method is combined with a high temperature melting technology.

The inner wall of the quartz tube with an outer diameter of 13 mm and a length of 220 mm is treated for 2 h by using 20% of HF solution; meanwhile, a mixed solution of 0.1555 g of $Ce(NO_3)_2.6H_2O$, 33 mL of tetraethoxysilane TEOS and 50 mL of deionized water is prepared; after uniformly stirred, 4 mL is taken and coated on the HF etched inner wall of the quartz tube; subsequently, treatment is made in an oven under a temperature of 90° C. for 3 h; finally, under a temperature of 2000° C. and 1.1 bars of pure oxygen atmosphere, the material is melted for 30 minutes; then, a dopant thin layer with a thickness of 180 nm is formed on the inner wall of the reaction section; and the material is cooled naturally to obtain the reaction section AE of a Ce© catalytic quartz reactor with a diameter of 13 mm and a length of 220 mm, wherein the doping amount of Ce is 0.5 wt. %.

Embodiment 32

A sol-gel method is combined with a high temperature melting technology.

The inner wall of the quartz tube with an outer diameter of 25 mm and a length of 200 mm is treated for 2 h by using 20% of HF solution; meanwhile, a mixed solution of 0.082 g of Ga(NO$_3$)$_2$.6H$_2$O, 33 mL of tetraethoxysilane TEOS and 50 mL of deionized water is prepared; after uniformly stirred, 4 mL is taken and coated on the HF etched inner wall of the quartz tube; subsequently, treatment is made in an oven under a temperature of 90° C. for 3 h; finally, under a temperature of 2100° C. and 1.1 bars of pure oxygen atmosphere, the material is melted for 40 minutes; then, a dopant thin layer with a thickness of 180 nm is formed on the inner wall of the reaction section; and the material is cooled naturally to obtain the reaction section AF of a Ga© catalytic quartz reactor with a diameter of 25 mm and a length of 200 mm, wherein the doping amount of Ga is 0.4 wt. %.

Embodiment 33

A sol-gel method is combined with a high temperature melting technology.

The inner wall of the quartz tube with an outer diameter of 30 mm and a length of 170 mm is treated for 2 h by using 20% of HF solution; meanwhile, a mixed solution of 0.5344 g of Mg(NO$_3$)$_2$.6H$_2$O, 0.3688 g of Fe(NO$_3$)$_3$.9H$_2$O, 33 mL of tetraethoxysilane TEOS and 50 mL of deionized water is prepared; after uniformly stirred, 4 mL is taken and coated on the HF etched inner wall of the quartz tube; subsequently, treatment is made in an oven under a temperature of 90° C. for 3 h; finally, under a temperature of 2050° C. and 1.2 bars of air atmosphere, the material is melted for 50 minutes; then, a dopant thin layer with a thickness of 180 nm is formed on the inner wall of the reaction section; and the material is cooled naturally to obtain the reaction section AG of a Fe—Mg© catalytic quartz reactor with a diameter of 30 mm and a length of 170 mm, wherein the doping amounts of Fe and Mg are 0.4 wt. % and 0.6 wt. %.

Embodiment 34

A sol-gel method is combined with a high temperature melting technology.

The inner wall of the quartz tube with an outer diameter of 25 mm is treated for 2 h by using 20% of HF solution; meanwhile, a mixed solution of 0.5344 g and 0.3688 g of Fe(NO$_3$)$_3$.9H$_2$O, 0.1559 g of La(NO$_3$)$_2$.6H$_2$O, 33 mL of tetraethoxysilane TEOS and 50 mL of deionized water is prepared; after uniformly stirred, 4 mL is taken and coated on the HF etched inner wall of the quartz tube; subsequently, treatment is made in an oven under a temperature of 90° C. for 3 h; finally, under a temperature of 2050° C. and normal pressure air atmosphere, the material is melted for 60 minutes; then, a dopant thin layer with a thickness of 220 nm is formed on the inner wall of the reaction section; and the material is cooled naturally to obtain the reaction section AH of a Mg© catalytic quartz reactor with a diameter of 25 mm and a length of 200 mm, wherein the doping amount of Mg is 0.3 wt. %.

Embodiment 35

A sol-gel method is combined with a high temperature melting technology.

The inner wall of the quartz tube with an outer diameter of 20 mm and a length of 200 mm is treated for 2 h by using 2M of NaOH solution; meanwhile, a mixed solution of 0.3688 g of Fe(NO$_3$)$_3$.9H$_2$O, 33 mL of tetraethoxysilane TEOS and 50 mL of deionized water is prepared; after uniformly stirred, 4 mL is taken and coated on the HF etched inner wall of the quartz tube; subsequently, treatment is made in an oven under a temperature of 90° C. for 3 h; finally, under a temperature of 2050° C. and normal pressure argon atmosphere, the material is melted for 60 minutes; then, a dopant thin layer with a thickness of 100 nm is formed on the inner wall of the reaction section; and the material is cooled naturally to obtain the reaction section AI of a Fe© catalytic quartz reactor with a diameter of 20 mm and a length of 200 mm, wherein the doping amount of Fe is 0.6 wt. %.

Embodiment 36

A sol-gel method is combined with a high temperature melting technology.

The inner wall of the quartz tube with an outer diameter of 16 mm and a length of 300 mm is treated for 2 h by using 2M of NaOH solution; meanwhile, a mixed solution of 0.5344 g of Mg(NO$_3$)$_2$.6H$_2$O, 33 mL of tetraethoxysilane TEOS and 50 mL of deionized water is prepared; after uniformly stirred, 4 mL is taken and coated on the HF etched inner wall of the quartz tube; subsequently, treatment is made in an oven under a temperature of 90° C. for 3 h; finally, under a temperature of 2000° C. and normal pressure argon atmosphere, the material is melted for 60 minutes; then, a dopant thin layer with a thickness of 1 micrometer is formed on the inner wall of the reaction section; and the material is cooled naturally to obtain the reaction section AJ of a Mg© catalytic quartz reactor with a diameter of 16 mm and a length of 300 mm, wherein the doping amount of Mg is 0.2 wt. %.

Embodiment 37

A sol-gel method is combined with a high temperature melting technology.

The inner wall of the quartz tube with an outer diameter of 13 mm and a length of 200 mm is treated for 2 h by using 2M of NaOH solution; meanwhile, a mixed solution of 0.2288 g of Zn(NO$_3$)$_2$.6H$_2$O, 33 mL of tetraethoxysilane TEOS and 50 mL of deionized water is prepared; after uniformly stirred, 4 mL is taken and coated on the HF etched inner wall of the quartz tube; subsequently, treatment is made in an oven under a temperature of 90° C. for 3 h; finally, under a temperature of 2100° C. and 1.1 bars of argon atmosphere, the material is melted for 60 minutes; then, a dopant thin layer with a thickness of 800 nm is formed on the inner wall of the reaction section; and the material is cooled naturally to obtain the reaction section AK of a Zn© catalytic quartz reactor with a diameter of 13 mm and a length of 200 mm, wherein the doping amount of Zn is 0.45 wt. %.

Embodiment 38

A sol-gel method is combined with a high temperature melting technology.

The inner wall of the quartz tube with an outer diameter of 30 mm and a length of 300 mm is treated for 2 h by using 2M of NaOH solution; meanwhile, a mixed solution of 0.1559 g of La(NO$_3$)$_2$.6H$_2$O, 33 mL of tetraethoxysilane TEOS and 50 mL of deionized water is prepared; after uniformly stirred, 4 mL is taken and coated on the HF etched inner wall of the quartz tube; subsequently, treatment is made in an oven under a temperature of 90° C. for 3 h; finally, under a temperature of 2100° C. and 1.2 bars of argon atmosphere, the material is melted for 60 minutes;

then, a dopant thin layer with a thickness of 500 nm is formed on the inner wall of the reaction section; and the material is cooled naturally to obtain the reaction section AL of a La© catalytic quartz reactor with a diameter of 30 mm and a length of 300 mm, wherein the doping amount of La is 0.6 wt. %.

Embodiment 39

A sol-gel method is combined with a high temperature melting technology.

The inner wall of the quartz tube with an outer diameter of 10 mm and a length of 50 mm is treated for 2 h by using 2M of NaOH solution; meanwhile, a mixed solution of 0.1555 g of $Ce(NO_3)_2 \cdot 6H_2O$, 33 mL of tetraethoxysilane TEOS and 50 mL of deionized water is prepared; after uniformly stirred, 4 mL is taken and coated on the HF etched inner wall of the quartz tube; subsequently, treatment is made in an oven under a temperature of 90° C. for 3 h; finally, under a temperature of 2000° C. and 1.1 bars of argon atmosphere, the material is melted for 50 minutes; then, a dopant thin layer with a thickness of 600 nm is formed on the inner wall of the reaction section; and the material is cooled naturally to obtain the reaction section AM of a Ce© catalytic quartz reactor with a diameter of 10 mm and a length of 50 mm, wherein the doping amount of Ce is 0.55 wt. %.

Embodiment 40

A sol-gel method is combined with a high temperature melting technology.

The inner wall of the quartz tube with an outer diameter of 17 mm and a length of 50 mm is treated for 2 h by using 2M of NaOH solution; meanwhile, a mixed solution of 0.082 g of $Ga(NO_3)_2 \cdot 6H_2O$, 33 mL of tetraethoxysilane TEOS and 50 mL of deionized water is prepared; after uniformly stirred, 4 mL is taken and coated on the HF etched inner wall of the quartz tube; subsequently, treatment is made in an oven under a temperature of 90° C. for 3 h; finally, under a temperature of 2000° C. and 1.1 bars of helium atmosphere, the material is melted for 50 minutes; then, a dopant thin layer with a thickness of 300 nm is formed on the inner wall of the reaction section; and the material is cooled naturally to obtain the reaction section AN of a Ga© catalytic quartz reactor with a diameter of 17 mm and a length of 50 mm, wherein the doping amount of Ga is 0.35 wt. %.

Embodiment 41

A sol-gel method is combined with a high temperature melting technology.

The inner wall of the quartz tube with an outer diameter of 25 mm and a length of 330 mm is treated for 2 h by using 2M of NaOH solution; meanwhile, a mixed solution of 0.5344 g of $Mg(NO_3)_2 \cdot 6H_2O$, 0.3688 g of $Fe(NO_3)_3 \cdot 9H_2O$, 33 mL of tetraethoxysilane TEOS and 50 mL of deionized water is prepared; after uniformly stirred, 4 mL is taken and coated on the HF etched inner wall of the quartz tube; subsequently, treatment is made in an oven under a temperature of 90° C. for 3 h; finally, under a temperature of 2100° C. and 1.1 bars of helium atmosphere, the material is melted for 50 minutes; then, a dopant thin layer with a thickness of 750 nm is formed on the inner wall of the reaction section; and the material is cooled naturally to obtain the reaction section AO of a Fe—Mg© catalytic quartz reactor with a diameter of 25 mm and a length of 330 mm, wherein the doping amounts of Fe and Mg are 0.35 wt. % and 0.45 wt. %.

Embodiment 42

A sol-gel method is combined with a high temperature melting technology.

The inner wall of the quartz tube with an outer diameter of 25 mm and a length of 330 mm is treated for 2 h by using superfine SiC particles with 80-100 meshes to coarsen the inner surface of the quartz tube; meanwhile, a mixed solution of 0.5344 g and 0.3688 g of $Fe(NO_3)_3 \cdot 9H_2O$, 0.1559 g of $La(NO_3)_2 \cdot 6H_2O$, 33 mL of tetraethoxysilane TEOS and 50 mL of deionized water is prepared; after uniformly stirred, 4 mL is taken and coated on the HF etched inner wall of the quartz tube; subsequently, treatment is made in an oven under a temperature of 90° C. for 3 h; finally, under a temperature of 2000° C. and 1.2 bars of helium atmosphere, the material is melted for 60 minutes; then, a dopant thin layer with a thickness of 150 nm is formed on the inner wall of the reaction section; and the material is cooled naturally to obtain the reaction section AP of a Fe—La© catalytic quartz reactor with a diameter of 25 mm and a length of 330 mm, wherein the doping amounts of Fe and La are 0.4 wt. % and 0.5 wt. %.

2. Characterization of Inner Wall of Reaction Section of Catalytic Reactor

1) Inductively Coupled Plasma Atomic Emission Spectrometry (ICP-AES) Characterization The ICP-AES acid leaching (nitric acid and HF acid) method is used. The so-called ICP-AES acid leaching process is that the metal on the surface of the support can be dissolved by an acid leaching process if the metal is loaded on the surface of the support (the acid can only dissolve the metal component, but the metal oxide component cannot dissolve the support); degree of acid leaching (i.e., a ratio of surface loadings to surface loading and doping amount) can be obtained through ICP measurement; however, if the metallic elements cannot be dissolved by acid, it indicates that the metallic elements are doped in the Si-based support lattice and protected. Firstly, the reaction section A of the Fe©catalytic quartz reactor with a diameter of 20 mm is leached by dilute nitric acid, and the ICP analysis results show that no Fe ion is dissolved, and further indicate that all of Fe ions enter the lattice of Si-based substrate. However, if HF acid is adopted, not only the Si-based substrate can be dissolved, but also the metal components can be dissolved. The ICP analysis results show that all of Fe ions are dissolved, and the amount is just converted into the doping amount. The above analysis results show that all of Fe ions have been doped inside the lattice of Si-based substrate, and almost no Fe can be detected on the surface of Si-based substrate.

Figure 3:
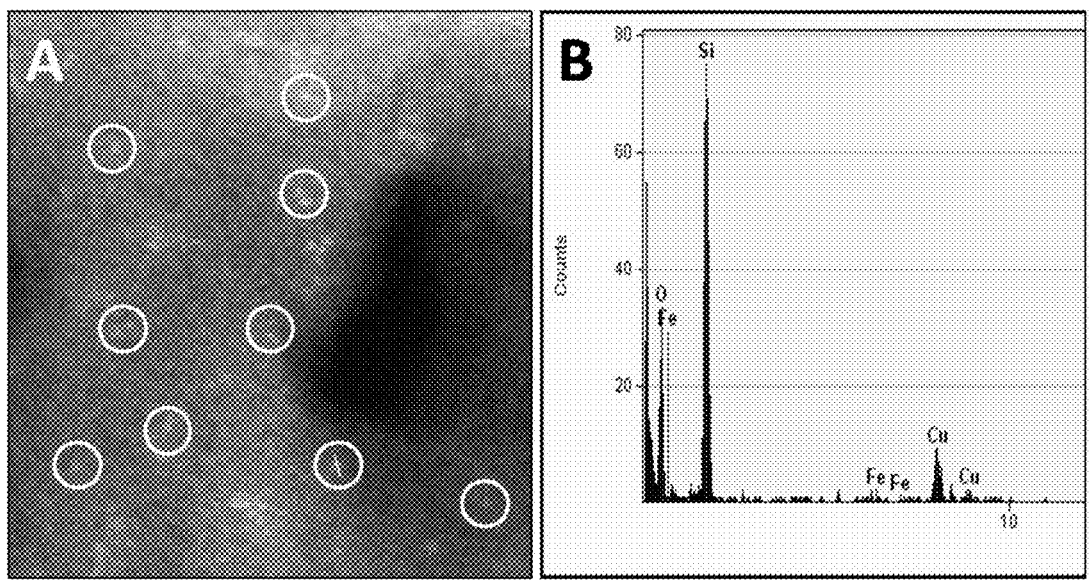
FIG. 3 characterizes HAADF-STEM high-resolution electron microscope and EDX of Fe-catalyst-quartz reactor A with a diameter of 20 mm.

2) Characterization of HAADF-STEM High-Resolution Electron Microscope and EDX of Reaction Section A of Fe© Catalytic Quartz Reactor with a Diameter of 20 mm A in FIG. 3 represents a single atom electron microscopic photo of the reaction section A (in embodiment 1 for preparation of the reaction section of the catalytic reactor) of the Fe© catalytic quartz reactor with a diameter of 20 mm. It can be seen from the electron microscopic characterization result by A in FIG. 3 that white circles are the single atom doped Fe metal atoms. EDX (B in FIG. 3) further confirms that these white points are single atom Fe species. Other elements, such as Cu, are from Cu grilles. Moreover, in the total electron microscopic photo, catalysts present an amorphous form with long-range disorder and short-range disorder.

3. Under the Oxygen-Free and Continuous Flow Conditions, Methane is Directly Converted to Olefin, Aromatic Hydrocarbon and Hydrogen All of the above catalytic reactors are directly used without loading the catalysts.

All of the reaction examples are achieved in a continuous flow micro-reaction apparatus, which is equipped with gas mass flow meters, gas deoxy and dehydration tubes, and online product analysis chromatography (The tail gas of the reactor is directly connected with the metering valve of chromatography, and periodic and real-time sampling and analysis will be achieved.). The reaction feed gas is composed of 10 vol. % $N_2$ and 90 vol. % $CH_4$ without specification, in which the nitrogen ($N_2$) is used as internal standard gas. To achieve the online product analysis, the Agilent 7890A chromatography with dual detectors of FID and TCD is used, wherein the FID detector with HP-1 capillary column is used to analyze the light olefin, light alkane and aromatic hydrocarbon; and the TCD detector with Hayesep D packed column is used to analyze the light olefin, light alkane, methane, hydrogen and internal standard $N_2$. According to the carbon balance before and after reaction, methane conversion, carbonic product selectivity and coke deposition are calculated by the method from the patents (CN1247103A and CN1532546A).

Embodiment 1

Figure 1:
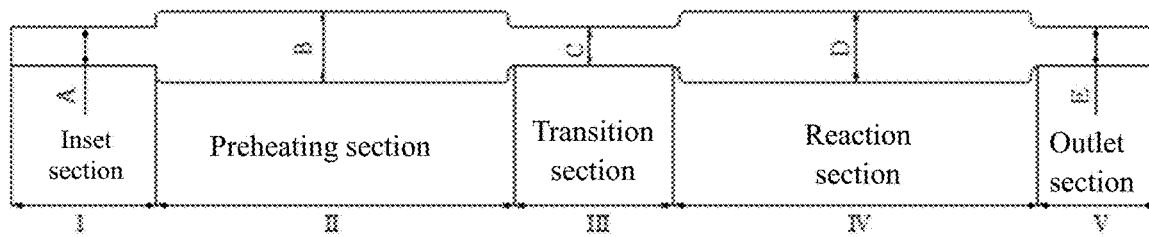
FIG. 1 is a configuration of a catalytic reactor of the present invention.

The reaction section A (with a diameter of 20 mm and a length of 100 mm) (embodiment 1 for preparation of the reaction section of the catalytic reactor) of the Fe© catalytic quartz reactor, the quartz preheating section (with a diameter of 8 mm and a length of 600 mm) and the quartz transition section (with a diameter of 14 mm and a length of 50 mm) are connected in accordance with FIG. 1 to form the catalytic quartz reactor. The air in the reactor is replaced with Ar gas of 30 ml/min for about 30 mins. A constant flow rate of Ar is maintained, and the reactor is programmed from room temperature up to 950° C. at a heating rate of 6° C./min. Meanwhile, the weight hourly space velocity (WHSV) of reaction feed gas is adjusted to 8.0 L/g/h. After the WHSV being kept for 30 mins, online analysis is started. The analysis results are as follows: 24% of methane conversion, 65% of ethylene selectivity, 10% of propylene selectivity, 20% of benzene selectivity and 5% of naphthalene selectivity, no coke deposition. For the 0.2 wt. % Fe©$SiO_2$ catalyst prepared by the method from patents 201310174960.5 and 201511003407.0, under the same condition, the analysis results show that: the methane conversion is higher than those of the first two methods by about 6-16%.

Embodiments 2-12

The reaction section J (with a diameter of 20 mm and a length of 250 mm) (embodiment 10 for preparation of the reaction section of the catalytic reactor) of the Ga—Al© catalytic quartz reactor, the quartz inlet section (with a diameter of 10 mm and a length of 100 mm), the quartz preheating section (with a diameter of 15 mm and a length of 300 mm), the transition section (with a diameter of 15 mm and a length of 50 mm) and the outlet section (with a diameter of 6 mm and a length of 100 mm) are connected in accordance with FIG. 1 to form the catalytic quartz reactor. The air in the reactor is replaced with Ar gas of 30 ml/min for about 30 mins. A constant flow rate of Ar is maintained, and the reactor is programmed from room temperature up to the following temperature and corresponding WHSV at a heating rate of 6° C./min. The WHSV of the reaction feed gas is adjusted to the following WHSV. The results of methane conversion and product selectivity are shown in the following table. For the 0.5 wt. % Ga-0.6 wt. % Al©$SiO_2$ catalyst prepared by the method from patents 201310174960.5 and 201511003407.0, under the same condition, the analysis results show that: the conversion is higher than those of the patents 201310174960.5 and 201511003407.0 by 2-15%.

| Embodiments | Temperature (° C.) | Hourly Space Velocity (L/g/h) | Methane Conversion Rate (%) | Ethylene Selectivity (%) | Propylene Selectivity (%) | Butylene Selectivity (%) | Benzene Selectivity (%) | Naphthalene Selectivity (%) |
|---|---|---|---|---|---|---|---|---|
| 2 | 750 | 1.6 | 4.2 | 77 | 6 | 0 | 15 | 2 |
| 3 | 850 | 2.2 | 6.3 | 75 | 8 | 0 | 14 | 3 |
| 4 | 900 | 3.6 | 10.2 | 73 | 8 | 0 | 15 | 4 |
| 5 | 950 | 4.8 | 19.5 | 73 | 5 | 6 | 16 | 0 |
| 6 | 960 | 6.0 | 21.3 | 72 | 8 | 4 | 15 | 1 |
| 7 | 970 | 7.2 | 24.5 | 70 | 7 | 0 | 18 | 5 |
| 8 | 980 | 8.4 | 26.8 | 70 | 6 | 6 | 15 | 3 |
| 9 | 990 | 9.6 | 29.2 | 68 | 8 | 5 | 18 | 1 |
| 10 | 1000 | 10.8 | 32.3 | 69 | 8 | 0 | 18 | 5 |
| 11 | 1010 | 12.0 | 37.5 | 66 | 9 | 0 | 20 | 5 |
| 12 | 1020 | 13.2 | 39.2 | 68 | 10 | 1 | 21 | 0 |

Embodiments 13-23

The reaction section O (with a diameter of 30 mm and a length of 200 mm) (embodiment 15 for preparation of the reaction section of the catalytic reactor) of the Mg—Mn—P© catalytic quartz reactor, the quartz preheating section (with a diameter of 15 mm and a length of 300 mm), the transition section (with a diameter of 15 mm and a length of 50 mm) and the outlet section (with a diameter of 6 mm and a length of 100 mm) are connected in accordance with FIG. 1 to form the catalytic quartz reactor. The air in the reactor is replaced with Ar gas of 45 ml/min for about 60 mins. A constant flow rate of Ar is maintained, and the reactor is programmed from room temperature up to the following temperature and corresponding WHSV at a heating rate of 6° C./min. The WHSV of the reaction feed gas is adjusted to the following WHSV. The results of methane conversion and product selectivity are shown in the following table. For the 0.6 wt. % Mg-0.5 wt. % Mn-0.7 wt. % P©SiO$_2$ catalyst prepared by the method from patents 201310174960.5 and 201511003407.0, under the same condition, the analysis results show that: the conversion of the present invention is higher than those of the patents 201310174960.5 and 201511003407.0 by 8-20%.

| Embod-iments | Temper-ature (° C.) | Hourly Space Velocity (L/g/h) | Methane Conversion Rate (%) | Ethylene Selectivity (%) | Propylene Selectivity (%) | Butylene Selectivity (%) | Benzene Selectivity (%) | Naphthalene Selectivity (%) |
|---|---|---|---|---|---|---|---|---|
| 13 | 750 | 3.2 | 3.4 | 76 | 6.5 | 0 | 16 | 1.5 |
| 14 | 850 | 4.2 | 5.5 | 74 | 8.5 | 0 | 15 | 2.5 |
| 15 | 900 | 5.6 | 9.4 | 72 | 8.5 | 0 | 16 | 3.5 |
| 16 | 950 | 6.8 | 18.7 | 72 | 5.5 | 6 | 16.5 | 0 |
| 17 | 960 | 8.0 | 20.5 | 71 | 8.5 | 4 | 16 | 0.5 |
| 18 | 970 | 9.2 | 23.7 | 69 | 7.5 | 0 | 19 | 4.5 |
| 19 | 980 | 10.4 | 26 | 69 | 6.5 | 6 | 16 | 2.5 |
| 20 | 990 | 11.2 | 28.4 | 67 | 8.5 | 5 | 19 | 0.5 |
| 21 | 1000 | 13.8 | 31.5 | 68 | 8.5 | 0 | 19 | 4.5 |
| 22 | 1010 | 15.6 | 36.7 | 65 | 9.5 | 0 | 21 | 4.5 |
| 23 | 1020 | 18.2 | 38.4 | 67 | 10.5 | 1 | 21.5 | 0 |

Embodiments 24-34

The reaction section L (with a diameter of 50 mm and a length of 1500 mm) (embodiment 12 for preparation of the reaction section of the catalytic reactor) of the La—Al—B© catalytic quartz reactor, the quartz preheating section (with a diameter of 15 mm and a length of 300 mm), the transition section (with a diameter of 15 mm and a length of 50 mm) and the outlet section (with a diameter of 6 mm and a length of 100 mm) are connected in accordance with FIG. 1 to form the catalytic quartz reactor. The air in the reactor is replaced with Ar gas of 80 ml/min for about 60 mins. A constant flow rate of Ar is maintained, and the reactor is programmed from room temperature up to the following temperature and corresponding WHSV at a heating rate of 6° C./min. The WHSV of the reaction feed gas is adjusted to the following WHSV. The results of methane conversion and product selectivity are shown in the following table. For the 0.2 wt. % La-0.4 wt. % Al-0.6 wt. % B©SiO$_2$ catalyst prepared by the method from patents 201310174960.5 and 201511003407.0, under the same condition, the analysis results show that: the conversion of the present invention is higher than those of the patents 201310174960.5 and 201511003407.0 by 8-20%.

Embodiment 35

The reaction section P (with a diameter of 30 mm and a length of 900 mm) (embodiment 17 for preparation of the reaction section of the catalytic reactor) of the Fe—Mn—Sn—Al—P© catalytic quartz reactor, the quartz inlet section (with a diameter of 8 mm and a length of 100 mm), the quartz preheating section (with a diameter of 15 mm and a length of 300 mm), the transition section (with a diameter of 15 mm and a length of 50 mm) and the outlet section (with a diameter of 6 mm and a length of 200 mm) are connected in accordance with FIG. 1 to form the catalytic quartz reactor. The air in the reactor is replaced with Ar gas of 30 ml/min for about 30 mins. A constant flow rate of Ar is maintained, and the reactor is programmed from room temperature up to 1020° C. at a heating rate of 6° C./min. Meanwhile, the weight hourly space velocity (WHSV) of reaction feed gas is adjusted to 20.5 L/g/h. After the WHSV being kept for 20 mins, online analysis is started, and the stability of the catalyst is studied for a long time. The analysis results are shown every 100 hours below, as shown in the following table. The methane conversion rate listed in the table is higher than those of the first two methods (compared with 0.4 wt. % Fe-0.3 wt. % Mn-0.2 wt. % Sn-0.45 wt. % Al-0.4 wt. % P©SiO$_2$ in 201310174960.5 and 201511003407.0 patents) by 12-20%, and the catalyst life is higher by about 500-700 hours.

| Embod-iments | Temper-ature (° C.) | Hourly Space Velocity (L/g/h) | Methane Conversion Rate (%) | Ethylene Selectivity (%) | Propylene Selectivity (%) | Butylene Selectivity (%) | Benzene Selectivity (%) | Naphthalene Selectivity (%) |
|---|---|---|---|---|---|---|---|---|
| 24 | 750 | 12 | 3.8 | 77.1 | 5.9 | 0 | 15 | 1.9 |
| 25 | 850 | 15 | 5.9 | 75.1 | 7.9 | 0 | 14 | 2.9 |
| 26 | 900 | 22 | 9.8 | 73.1 | 7.9 | 0 | 15 | 3.9 |
| 27 | 950 | 29 | 19.1 | 73.1 | 4.9 | 6 | 15.5 | 0.4 |
| 28 | 960 | 32 | 20.9 | 72.1 | 7.9 | 4 | 15 | 0.9 |
| 29 | 970 | 35 | 24.1 | 70.1 | 6.9 | 0 | 18 | 4.9 |
| 30 | 980 | 37 | 26.4 | 70.1 | 5.9 | 6 | 15 | 2.9 |
| 31 | 990 | 41 | 28.8 | 68.1 | 7.9 | 5 | 18 | 0.9 |
| 32 | 1000 | 42 | 31.9 | 69.1 | 7.9 | 0 | 18 | 4.9 |
| 33 | 1010 | 46 | 37.1 | 66.1 | 8.9 | 0 | 20 | 4.9 |
| 34 | 1020 | 50 | 38.8 | 68.1 | 9.9 | 1 | 20.5 | 0.4 |

| Time interval (hour) | Methane Conversion Rate (%) | Ethylene Selectivity (%) | Propylene Selectivity (%) | Butylene Selectivity (%) | Benzene Selectivity (%) | Naphthalene Selectivity (%) |
|---|---|---|---|---|---|---|
| 100 | 47.9 | 70 | 8 | 0 | 16 | 6 |
| 200 | 48.5 | 69 | 10 | 0 | 18 | 3 |
| 300 | 49.0 | 67 | 9 | 0 | 18 | 8 |
| 400 | 49.8 | 68 | 8 | 1 | 20 | 3 |
| 500 | 49.5 | 66 | 8 | 2 | 20 | 4 |
| 600 | 40.3 | 65 | 7 | 0 | 23 | 5 |
| 700 | 49.2 | 67 | 9 | 0 | 20 | 4 |
| 800 | 48.5 | 65 | 8 | 0 | 22 | 5 |
| 900 | 51 | 68 | 9 | 0 | 20 | 3 |
| 1000 | 49.8 | 69 | 8 | 0 | 21 | 2 |

Embodiment 36

The reaction section V (with a diameter of 30 mm and a length of 300 mm) (embodiment 21 for preparation of the reaction section of the catalytic reactor) of the Fe—Zn—P© catalytic silica carbide reactor, the quartz inlet section (with a diameter of 8 mm and a length of 100 mm), the quartz preheating section (with a diameter of 15 mm and a length of 260 mm), the transition section (with a diameter of 15 mm and a length of 60 mm) and the outlet section (with a diameter of 6 mm and a length of 250 mm) are connected in accordance with FIG. 1 to form the catalytic silica carbide reactor. The air in the reactor is replaced with Ar gas of 30 ml/min for about 30 mins. A constant flow rate of Ar is maintained, and the reactor is programmed from room temperature up to 1020° C. at a heating rate of 8° C./min. Meanwhile, the weight hourly space velocity (WHSV) of reaction feed gas is adjusted to 15 L/g/h. After the WHSV being kept for 30 mins, online analysis is started. The analysis results are as follows: 35% of methane conversion, 69% of ethylene selectivity, 15% of propylene and butylene selectivity, 10.0% of benzene selectivity and 6% of naphthalene selectivity. For the 0.6 wt. % Fe-0.5 wt. % Zn-0.35 wt. % P©SiO$_2$ catalyst prepared by the method from patents 201310174960.5 and 201511003407.0, under the same condition, the analysis results show that: the conversion of the present invention is higher than those of the two patents by 8%.

Embodiment 37

The reaction section W (with a diameter of 50 mm and a length of 600 mm) (embodiment 23 for preparation of the reaction section of the catalytic reactor) of the Fe—Zn—P© catalytic silica carbide reactor, the quartz inlet section (with a diameter of 8 mm and a length of 100 mm), the quartz preheating section (with a diameter of 15 mm and a length of 300 mm), the transition section (with a diameter of 15 mm and a length of 50 mm) and the outlet section (with a diameter of 6 mm and a length of 200 mm) are connected in accordance with FIG. 1 to form the catalytic silica carbide reactor. The air in the reactor is replaced with Ar gas of 80 ml/min for about 60 mins. A constant flow rate of Ar is maintained, and the reactor is programmed from room temperature up to 1020° C. at a heating rate of 6° C./min. Meanwhile, the weight hourly space velocity (WHSV) of reaction feed gas is adjusted to 27.8 L/g/h. After the WHSV being kept for 30 mins, online analysis is started. The analysis results are as follows: 35% of methane conversion, 70.0% of ethylene selectivity, 10.0% of benzene selectivity and 20% of naphthalene selectivity. For the 0.3 wt. % Fe-0.2 wt. % Zn-0.4 wt. % P©SiO$_2$ catalyst prepared by the method from patents 201310174960.5 and 201511003407.0, under the same condition, the analysis results show that: the conversion of the present invention is higher than those of the two patents by 10%.

Embodiment 38

The reaction section X (with a diameter of 20 mm and a length of 360 mm) (embodiment 24 for preparation of the reaction section of the catalytic reactor) of the Fe—Zn—P© catalytic silica carbide reactor, the quartz inlet section (with a diameter of 8 mm and a length of 100 mm), the quartz preheating section (with a diameter of 15 mm and a length of 400 mm), the transition section (with a diameter of 15 mm and a length of 60 mm) and the outlet section (with a diameter of 6 mm and a length of 200 mm) are connected in accordance with FIG. 1 to form the catalytic SiO$_2$ coated silica carbide reactor. The air in the reactor is replaced with Ar gas of 30 ml/min for about 30 mins. A constant flow rate of Ar is maintained, and the reactor is programmed from room temperature up to 1020° C. at a heating rate of 6° C./min. Meanwhile, the weight hourly space velocity (WHSV) of reaction feed gas is adjusted to 19.8 L/g/h. After the WHSV being kept for 30 mins, online analysis is started. The analysis results are as follows: 37% of methane conversion, 77.0% of ethylene selectivity, 15.0% of propylene and butylene selectivity and 7.0% of benzene selectivity. For the 0.4 wt. % Fe-0.3 wt. % Zn-0.2 wt. % P©SiO$_2$ catalyst prepared by the method from patents 201310174960.5 and 201511003407.0, under the same condition, the analysis results show that: the conversion of the present invention is higher than those of the two patents by 11%.

Embodiment 39

The reaction section AA (with a diameter of 13 mm and a length of 100 mm) (embodiment 27 for preparation of the reaction section of the catalytic reactor) of the Fe© catalytic quartz reactor, the quartz preheating section (with a diameter of 15 mm and a length of 600 mm), the transition section (with a diameter of 15 mm and a length of 60 mm) and the outlet section (with a diameter of 6 mm and a length of 100 mm) are connected in accordance with FIG. 1 to form the catalytic quartz reactor. The air in the reactor is replaced with Ar gas of 30 ml/min for about 30 mins. A constant flow rate of Ar is maintained, and the reactor is programmed from room temperature up to 950° C. at a heating rate of 6° C./min. Meanwhile, the weight hourly space velocity (WHSV) of reaction feed gas is adjusted to 4.8 L/g/h. After the WHSV being kept for 30 mins, online analysis is started. The analysis results are as follows: 13.4% of methane conversion, 44.2% of ethylene selectivity, 15.0% of propylene and butylene selectivity and 23.0% of benzene selectivity. For the 0.5 wt. % Fe©SiO$_2$ catalyst prepared by the method from patents 201310174960.5 and 201511003407.0, under the same condition, the analysis results show that: the conversion of the present invention is higher than those of the two patents by 4%.

Embodiment 40

The reaction section AC (with a diameter of 20 mm and a length of 200 mm) (embodiment 29 for preparation of the reaction section of the catalytic reactor) of the Zn© catalytic quartz reactor, the quartz inlet section (with a diameter of 15 mm and a length of 60 mm), the quartz preheating section (with a diameter of 20 mm and a length of 600 mm), the transition section (with a diameter of 15 mm and a length of 60 mm) and the outlet section (with a diameter of 6 mm and a length of 100 mm) are connected in accordance with the figure to form the catalytic quartz reactor. The air in the reactor is replaced with Ar gas of 30 ml/min for about 30 mins. A constant flow rate of Ar is maintained, and the reactor is programmed from room temperature up to 950° C. at a heating rate of 6° C./min. Meanwhile, the weight hourly space velocity (WHSV) of reaction feed gas is adjusted to 4.8 L/g/h. After the WHSV being kept for 30 mins, online analysis is started. The analysis results are as follows: 12.4% of methane conversion, 48.2% of ethylene selectivity, 6.0% of propylene and butylene selectivity and 22.0% of benzene selectivity. For the 0.5 wt. % Zn©SiO$_2$ catalyst prepared by the method from patents 201310174960.5 and 201511003407.0, under the same condition, the analysis results show that: the conversion of the present invention is higher than those of the two patents by 3%.

Embodiment 41

The reaction section AD (with a diameter of 20 mm and a length of 250 mm) (embodiment 30 for preparation of the reaction section of the catalytic reactor) of the La© catalytic quartz reactor, the quartz inlet section (with a diameter of 10 mm and a length of 60 mm), the quartz preheating section (with a diameter of 15 mm and a length of 600 mm), the transition section (with a diameter of 15 mm and a length of 60 mm) and the outlet section (with a diameter of 6 mm and a length of 100 mm) are connected in accordance with FIG. 1 to form the catalytic quartz reactor. The air in the reactor is replaced with Ar gas of 30 ml/min for about 30 mins. A constant flow rate of Ar is maintained, and the reactor is programmed from room temperature up to 950° C. at a heating rate of 6° C./min. Meanwhile, the weight hourly space velocity (WHSV) of reaction feed gas is adjusted to 4.8 L/g/h. After the WHSV being kept for 30 mins, online analysis is started. The analysis results are as follows: 13.4% of methane conversion, 41.2% of ethylene selectivity, 4.0% of propylene and butylene selectivity and 21.0% of benzene selectivity. For the 0.6 wt. % LaOSiO$_2$ catalyst prepared by the method from patents 201310174960.5 and 201511003407.0, under the same condition, the analysis results show that: the conversion of the present invention is higher than those of the two patents by 4%.

Embodiment 42

The reaction section AL (with a diameter of 30 mm and a length of 300 mm) (embodiment 38 for preparation of the reaction section of the catalytic reactor) of the La© catalytic quartz reactor, the quartz inlet section (with a diameter of 14 mm and a length of 60 mm), the quartz preheating section (with a diameter of 20 mm and a length of 500 mm), the transition section (with a diameter of 15 mm and a length of 60 mm) and the outlet section (with a diameter of 6 mm and a length of 100 mm) are connected in accordance with FIG. 1 to form the catalytic quartz reactor. The La©SiO$_2$-coated quartz reactor AL with a diameter of 30 mm is used. The air in the reactor is replaced with Ar gas of 30 ml/min for about 30 mins. A constant flow rate of Ar is maintained, and the reactor is programmed from room temperature up to 950° C. at a heating rate of 6° C./min. Meanwhile, the weight hourly space velocity (WHSV) of reaction feed gas is adjusted to 4.8 L/g/h. After the WHSV being kept for 30 mins, online analysis is started. The analysis results are as follows: 14.4% of methane conversion, 46.2% of ethylene selectivity, 7.0% of propylene and butylene selectivity and 24.0% of benzene selectivity. For the 0.6 wt. % La©SiO$_2$ catalyst prepared by the method from patents 201310174960.5 and 201511003407.0, under the same condition, the analysis results show that: the conversion of the present invention is higher than those of the two patents by 5%.

Embodiment 43

The reaction section AL (with a diameter of 25 mm and a length of 330 mm) (embodiment 41 for preparation of the reaction section of the catalytic reactor) of the Fe—Mg © catalytic quartz reactor, the quartz inlet section (with a diameter of 14 mm and a length of 60 mm), the quartz preheating section (with a diameter of 20 mm and a length of 500 mm), the transition section (with a diameter of 15 mm and a length of 60 mm) and the outlet section (with a diameter of 6 mm and a length of 100 mm) are connected in accordance with FIG. 1 to form the catalytic quartz reactor. The air in the reactor is replaced with Ar gas of 30 ml/min for about 30 mins. A constant flow rate of Ar is maintained, and the reactor is programmed from room temperature up to 950° C. at a heating rate of 6° C./min. Meanwhile, the weight hourly space velocity (WHSV) of reaction feed gas is adjusted to 4.8 L/g/h. After the WHSV being kept for 30 mins, online analysis is started. The analysis results are as follows: 16.4% of methane conversion, 41.2% of ethylene selectivity, 11.0% of propylene and butylene selectivity and 20.0% of benzene selectivity. For the 0.35 wt. % Fe-0.45 wt. % Mg©SiO$_2$ catalyst prepared by the method from patents 201310174960.5 and 201511003407.0, under the same condition, the analysis results show that: the conversion of the present invention is higher than those of the two patents by 8%.

Embodiment 44

The reaction section J (with a diameter of 20 mm and a length of 300 mm) (embodiment 6 for preparation of the reaction section of the catalytic reactor) of the Fe—Zn—P© catalytic quartz reactor, the quartz inlet section (with a diameter of 10 mm and a length of 100 mm), the quartz preheating section (with a diameter of 20 mm and a length of 500 mm), the transition section (with a diameter of 15 mm and a length of 50 mm) and the outlet section (with a diameter of 6 mm and a length of 100 mm) are connected in accordance with FIG. 1 to form the catalytic quartz reactor. The air in the reactor is replaced with Ar gas of 30 ml/min for about 30 mins. A constant flow rate of Ar is maintained, and the reactor is programmed from room temperature up to 950° C. at a heating rate of 6° C./min. Meanwhile, the weight hourly space velocity (WHSV) of reaction feed gas (5 vol. % $CO_2$, 85 vol. % $CH_4$, 10 vol. % $N_2$) is adjusted to 9.0 L/g/h. After the WHSV being kept for 30 mins, online analysis is started. The analysis results are as follows: 21.0% of methane conversion, 69% of ethylene selectivity, 10% of propylene selectivity, 18% of benzene selectivity and 3% of naphthalene selectivity. For the 0.7 wt. % Fe-0.6 wt. % Zn-0.8 wt. % P©SiO$_2$ catalyst prepared by the method from patents 201310174960.5 and 201511003407.0, under the same condition, the analysis results show that: the conversion of the present invention is higher than those of the two patents by 10%.

Embodiment 45

The reaction section J (with a diameter of 20 mm and a length of 300 mm) (embodiment 6 for preparation of the reaction section of the catalytic reactor) of the Fe—Zn—P© catalytic quartz reactor, the quartz inlet section (with a diameter of 10 mm and a length of 100 mm), the quartz preheating section (with a diameter of 20 mm and a length of 500 mm), the transition section (with a diameter of 15 mm and a length of 50 mm) and the outlet section (with a diameter of 6 mm and a length of 100 mm) are connected in accordance with FIG. 1 to form the catalytic quartz reactor. The air in the reactor is replaced with Ar gas of 30 ml/min for about 30 mins. A constant flow rate of Ar is maintained, and the reactor is programmed from room temperature up to 950° C. at a heating rate of 6° C./min. Meanwhile, the weight hourly space velocity (WHSV) of reaction feed gas (5 vol. % $H_2O$, 85 vol. % $CH_4$, 10 vol. % $N_2$) is adjusted to 8.0 L/g/h. After the WHSV being kept for 30 mins, online analysis is started. The analysis results are as follows: 24.2% of methane conversion, 74% of ethylene selectivity, 6% of propylene selectivity, and 20% of benzene selectivity. For the 0.7 wt. % Fe-0.6 wt. % Zn-0.8 wt. % P©$SiO_2$ catalyst prepared by the method from patents 201310174960.5 and 201511003407.0, under the same condition, the analysis results show that: the conversion of the present invention is higher than those of the two patents by 10%.

Embodiment 46

The reaction section J (with a diameter of 20 mm and a length of 300 mm) (embodiment 6 for preparation of the reaction section of the catalytic reactor) of the Fe—Zn—P© catalytic quartz reactor, the quartz inlet section (with a diameter of 10 mm and a length of 100 mm), the quartz preheating section (with a diameter of 20 mm and a length of 500 mm), the transition section (with a diameter of 15 mm and a length of 50 mm) and the outlet section (with a diameter of 6 mm and a length of 100 mm) are connected in accordance with FIG. 1 to form the catalytic quartz reactor. The air in the reactor is replaced with Ar gas of 30 ml/min for about 30 mins. A constant flow rate of Ar is maintained, and the reactor is programmed from room temperature up to 950° C. at a heating rate of 6° C./min. Meanwhile, the weight hourly space velocity (WHSV) of reaction feed gas (2 vol. % $C_2H_6$, 85 vol. % $CH_4$, 10 vol. % $N_2$) is adjusted to 9.0 L/g/h. After the WHSV being kept for 30 mins, online analysis is started. The analysis results are as follows: 26% of methane conversion, 73% of ethylene selectivity, 10% of benzene selectivity and 17% of naphthalene selectivity. For the 0.7 wt.þ -0.6 wt. % Zn-0.8 wt. % P©$SiO_2$ catalyst prepared by the method from patents 201310174960.5 and 201511003407.0, under the same condition, the analysis results show that: the conversion of the present invention is higher than those of the two patents by 11%.

In summary, under the pattern in the catalytic reactor of the present invention, reaction temperature is 750-1100° C.; reaction pressure is normal pressure; the weight hourly space velocity of methane is 1.0-30.0 L/g/h; methane conversion is 10-70%; ethylene selectivity is 60-95%; propylene and butylene selectivities are 5-25%; and aromatic hydrocarbon selectivity is 0-25%.

It is concluded that the present invention has the characteristics of long catalyst life (>500 hrs) of the catalytic reactor, high stability of redox and hydrothermal properties under high temperature (<1400° C.), high product selectivity, zero coke deposition, easy separation of products, good process reproducibility, safe and reliable operation, etc., and has wide industrial application prospect.

It should be noted that in accordance with the above embodiments of the present invention, those skilled in the art can completely realize the full scope of independent claims and dependent claims of the present invention; the realization processes and methods are the same as those of the above embodiments; and a part not described in detail in the present invention belongs to a widely-known technology in the field.

The above is just part of concrete implementation manners of the present invention, but the protection scope of the present invention is not limited thereto. Any change or replacement contemplated easily by those skilled in the art familiar with the technical field within the technical scope disclosed by the present invention shall be covered within the protection scope of the present invention.

We claim:

1. A catalytic reactor, comprising a preheating section and a reaction section, wherein the reaction section comprises a quartz tube or a silica carbide tube, wherein the quartz tube or the silica carbide tube has an inner wall that is directly lattice-doped with a catalytically active component or coated with a Si-based material, wherein the Si-based material is lattice-doped by the catalytically active component, to form a dopant thin layer, whereby a feed raw material enters the preheating section first before entering the reaction section.

2. The catalytic reactor according to claim 1, wherein the length II of the preheating section and the length IV of the reaction section are respectively 50-2000 mm.

3. The catalytic reactor configuration according to claim 1, wherein the thickness of the dopant thin layer is 1 nm-1 mm.

4. The catalytic reactor according to claim 1, wherein the catalytically active component is selected from the group consisting of metallic elements, nonmetallic elements, and combinations thereof.

5. The catalytic reactor according to claim 4, wherein the metallic elements comprise: lithium, magnesium, aluminum, calcium, strontium, barium, titanium, manganese, vanadium, chromium, iron, cobalt, nickel, zinc, germanium, tin, gallium, zirconium, gold, lanthanum, cerium, praseodymium, neodymium, europium, erbium, and ytterbium.

6. The catalytic reactor according to claim 4, wherein the nonmetallic elements comprise: boron and phosphorus.

7. A preparation method for a reaction section in a catalytic reactor, through a modified chemical vapor deposition (MCVD) method which is one of the following three methods:

the first method: at 1-3 atmospheric pressure, bringing silicon tetrachloride liquid under the drive of support gas or bringing the silicon tetrachloride liquid and nonmetallic chloride which is gas-phase doped at 50-500° C. under the drive of the support gas to enter an MCVD apparatus to react with oxygen at 1400-1650° C.; conducting vapor deposition of silicon-based thin layer with a thickness of 0.01-100 micrometers on the inner wall of the reaction section; subsequently immersing the reaction section at 20-80° C. into metal salt doped aqueous solution for 0.1-20 hours; then melting the immersed reaction section at 1800-2200° C. to obtain the corresponding metal lattice doped reaction section; forming a dopant thin layer with a thickness of 1 nm-1 mm on the inner wall of the reaction section; then immediately cooling; and curing to obtain the reaction section with catalytic activity;

the second method: at 1-3 atmospheric pressure, bringing silicon tetrachloride liquid and gas-phase-doped volatile metal salt which is gasified at 50-950° C. under the drive of support gas or bringing the silicon tetrachloride liquid, the gas-phase-doped volatile metal salt which is gasified at 50-950° C. and nonmetallic chloride which is gas-phase doped at 50-500° C. under the drive of the support gas to enter an MCVD apparatus to react with oxygen at 1400-1650° C.; conducting vapor deposition on the inner wall of the reaction section for 10 min-2 hour; subsequently melting at 1800-2200° C. to obtain the corresponding metal lattice doped reaction section; forming a dopant thin layer with a thickness of 1 nm-1 mm on the inner wall of the reaction section; then immediately cooling; and curing to obtain the reaction section with catalytic activity;

the third method: at 1-3 atmospheric pressure, bringing silicon tetrachloride liquid and normal-temperature liquid metal chloride or normal-temperature liquid nonmetallic chloride or oxygen chloride under the drive of support to enter an MCVD apparatus to react with oxygen at 1400-1650° C.; conducting vapor deposition on the inner wall of the reaction section for 10 min-2 hour; subsequently melting at 1800-2200° C. to obtain the corresponding metal lattice doped reaction section; forming a dopant thin layer with a thickness of 1 nm-1 mm on the inner wall of the reaction section; then immediately cooling; and curing to obtain the reaction section with catalytic activity.

8. A preparation method for a reaction section in a catalytic reactor, wherein the reactor adopts sol gel combined with a melting technology, the reaction section comprises an inner wall, and the method comprises: at room temperature, etching the inner wall of the reaction section for 1-48 hours using HF or NaOH solution, or grinding the inner wall of the reaction section is ground for 0.5-4 h using silicon-based particles of 40-100 meshes; preparing a mixed solution of metal salt, silicate and water; covering the mixed solution uniformly on the inner wall of the etched reaction section; conducting sol-gel reaction at 20-120° C. for 0.2-96 h; melting at 1800-2200° C. to obtain a corresponding metal lattice doped reaction section inner wall; then conducting immediate cooling; and curing to obtain the reactor with catalytic function.

9. The preparation method according to claim 7, wherein the metal salt in the first method is at least one of nitrate, soluble halogenide, soluble sulphate, soluble carbonate, soluble calcium phosphate, soluble organic alkoxide with C number of 1-2, and organic acid salt with C number of 1-2.

10. The preparation method according to claim 7, wherein the metal salt in the second method is at least one of metal chloride, organic alkoxide of C number of 1-2, and organic acid salt of C number of 1-2.

11. The preparation method according to claim 7, wherein the normal-temperature liquid metal chloride in the third method is at least one of tin tetrachloride, titanium tetrachloride and germanium tetrachloride; and the normal-temperature liquid nonmetallic chloride or oxygen chloride is at least one of boron trichloride and phosphorous oxychloride.

12. The preparation method according to claim 8, wherein the silicate is at least one of tetramethyl orthosilicate, tetraethoxysilane, tetrapropyl orthosilicate, isopropyl silicate, tetrabutyl orthosilicate and trimethylsiloxysilicate.

13. The preparation method according to claim 8, wherein the content ratio of the metal salt to the silicate is 1:1000 to 1:1, and the content ratio of the silicate to water is 1:0.1 to 1:10.

14. The preparation method according to claim 8, wherein in the sol-gel reaction process, the mass concentration of the metallic elements in the mixed solution of the metal salt, the silicate and the water is 50 ppm-10%; the treatment time of sol is 2-100 h; gel temperature is 10-120° C. and the treatment time of gel is 1-48 h.

15. The preparation method according to claim 8, wherein the preparation process of the first method comprises an immersing process, and the solubility of immersion liquid is 50 ppm-5%; immersion time is 0.1-24 h; and immersion temperature is 20-80° C.

16. The preparation method according to claim 7, wherein the thickness of the dopant thin layer is 1 nm-0.5 mm.

17. The preparation method according to claim 7, wherein in the preparation process of the catalyst, deposition time is 10 min-1 h.

18. The preparation method according to claim 7, wherein the flow velocity of the support gas is 5-2000 ml/min.

19. The preparation method according to claim 7, wherein a melting atmosphere is at least one of inert gas, air, and oxygen; the inert gas comprises one or more of helium, argon or nitrogen; melting time is 0.01-3 h.

20. The preparation method according to claim 7, wherein the cooling is gas cooling; a cooling rate is 50° C./s–2000° C./s; and the gas in the gas cooling is at least one of inert gases, nitrogen, oxygen, and air.

21. The preparation method according to claim 7, wherein the support gas is high purity oxygen with a volume concentration above 99.9999% or high purity helium with a volume concentration above 99.9999%.

22. The preparation method according to claim 7, wherein the catalyst layer on the inner wall of the reactor only comprises lattice doped metallic elements and supports no metal or metal compound on the surface.

23. A method of direct synthesis of ethylene through oxygen-free catalysis of methane comprising catalyzing and converting methane in a feed gas to ethylene in the catalytic reactor of claim 1.

24. The method of direct synthesis of ethylene through oxygen-free catalysis of methane according to claim 23, wherein the temperature of the catalytic reaction is 750-1200° C.

25. The method of direct synthesis of ethylene through oxygen-free catalysis of methane according to claim 23 further comprising, before conducting the reaction, a pretreatment process in a pretreatment atmosphere that is at least one of reaction feed gas, hydrogen or air at a temperature of 750-900° C., a pretreatment pressure of 0.1-1 Mpa, and a weight hourly space velocity of the reaction feed gas of 0.8-2.5 L/g/h.

26. The method of direct synthesis of ethylene through oxygen-free catalysis of methane according to claim 23, wherein the feed gas is methane gas or a gas mixture of methane and other gases;
  besides methane, the reaction feed gas comprises optionally one or two of other inert gases and non-inert gases; the inert gases comprise at least one of nitrogen, helium, neon, argon and krypton, and the volume content of inert gas in the reaction feed gas is 0-95%;
  the non-inert gases comprise at least one of carbon monoxide, hydrogen, carbon dioxide, water, and alkanes with 2 to 4 carbon atoms, and the volume ratio of non-inert gas to methane is 0-10%; and the volume content of methane in the reaction feed gas is 5-100%.

27. The method of direct synthesis of ethylene through oxygen-free catalysis of methane according to claim 23, wherein the step of catalyzing and converting methane is conducted at a pressure of 0.05-1 MPa; and a weight hourly space velocity of the reaction feed gas of 1.0-30.0 L/g/h.

28. The method of direct synthesis of ethylene through oxygen-free catalysis of methane according to claim 23, wherein the step of catalyzing and converting methane also produces byproduct comprising at least one of propylene, butylene, aromatic hydrocarbon, and hydrogen, and wherein the aromatic hydrocarbon comprises at least one of benzene, toluene, xylene, o-xylene, m-xylene, ethylbenzene, and naphthalene.

29. The catalytic reactor according to claim 1 further comprising at least one of the following sections: an inlet section located at the front of the preheating section, a transition section located between the preheating section and the reaction section, and an outlet section located at the rear of the reaction section.

30. The catalytic reactor according to claim 29 comprising each of the inlet section, preheating section, the transition section, the reaction section, and the outlet section, wherein the inner diameter A of the inlet section, the inner diameter B of the preheating section, the inner diameter C of the transition section, the inner diameter D of the reaction section, and the inner diameter E of the outlet section are respectively 3-500 mm.

31. The catalytic reactor configuration according to claim 29 comprising each of the inlet section, the transition section, and outlet section, wherein none of the length I of the inlet section, the length III of the transition section, and the length V of the outlet section is larger than 5000 mm, and 0<I+III+V<5000 mm.

32. The catalytic reactor configuration according to claim 29 comprising each of the inlet section, preheating section, the transition section, the reaction section, and the outlet section, wherein the length I of the inlet section, the length II of the preheating section, the length III of the transition section, the length IV of the reaction section, and the length V of the outlet section satisfy: 0.1 m<I+II+III+IV+V<10 m.

33. The catalytic reactor configuration according to claim 30, wherein the inner diameter of each section needs to satisfy: D>A=B=C=E, or D=B>A=C=E, or B>D>A=C=E, or D>B>A=C=E, or A=B>D>C=E, or A=B>D>C>E, or A=B=C=D=E, or A=E>B=C=D, or A=C=E>B=D.

* * * * *